United States Patent
Wolf

(10) Patent No.: US 10,192,038 B2
(45) Date of Patent: Jan. 29, 2019

(54) PROCESS FOR DETERMINING THE DISTILLATION CHARACTERISTICS OF A LIQUID PETROLEUM PRODUCT CONTAINING AN AZEOTROPIC MIXTURE

(71) Applicant: BUTAMAX ADVANCED BIOFUELS LLC, Wilmington, DE (US)

(72) Inventor: Leslie R. Wolf, Naperville, IL (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 380 days.

(21) Appl. No.: 15/220,188

(22) Filed: Jul. 26, 2016

(65) Prior Publication Data

US 2016/0335416 A1    Nov. 17, 2016

Related U.S. Application Data

(60) Continuation-in-part of application No. 15/179,469, filed on Jun. 10, 2016, which is a continuation of application No. 14/497,682, filed on Sep. 26, 2014, now Pat. No. 9,388,353, which is a division of application No. 13/162,206, filed on Jun. 16, 2011, now Pat. No. 8,876,924, application No. 15/220,188, which is a continuation-in-part of application No. 12/469,373, filed on May 20, 2009, now abandoned.

(60) Provisional application No. 61/355,222, filed on Jun. 16, 2010, provisional application No. 61/055,284, filed on May 22, 2008.

(51) Int. Cl.
| | |
|---|---|
| G06F 19/00 | (2018.01) |
| G06F 17/11 | (2006.01) |
| G06F 17/50 | (2006.01) |
| G01N 33/28 | (2006.01) |
| G01N 25/08 | (2006.01) |

(52) U.S. Cl.
CPC ....... *G06F 19/704* (2013.01); *G01N 33/2852* (2013.01); *G06F 17/11* (2013.01); *G06F 17/5009* (2013.01); *G01N 25/08* (2013.01)

(58) Field of Classification Search
CPC .... G06F 19/704; G06F 17/11; G06F 17/5009; G01N 33/2852; G01N 25/08
See application file for complete search history.

(56) References Cited

U.S. PATENT DOCUMENTS

| | | | |
|---|---|---|---|
| 5,755,833 | A | 5/1998 | Ishida et al. |
| 5,782,937 | A | 7/1998 | Colucci et al. |
| 5,858,028 | A | 1/1999 | Davies et al. |
| 5,997,592 | A | 12/1999 | Lin et al. |
| 6,083,228 | A | 7/2000 | Wolf |
| 6,248,142 | B1 | 6/2001 | Caprotti |
| 6,277,159 | B1 | 8/2001 | Caprotti et al. |
| 6,280,488 | B1 | 8/2001 | Dillworth et al. |
| 6,581,442 | B1 | 6/2003 | Abaev et al. |

(Continued)

OTHER PUBLICATIONS

Mair et al, Separation of Hydrocarbons by Azeotropic Distillation, 1941, Journal of Research of the National Bureau of Standards, vol. 27, pp. 39-63. (Year: 1941).*
American Petroleum Institute, Determination of the Potential Property Ranges of Mid-Level Ethanol Blends, Final Report, Apr. 23, 2010.
Horsley, Graphical Method for Predicting Azeotropism and Effect of Pressure on Azeotropic Constants, Advances in Chemistry; American Chemical Society: Washington, DC, 1973, pp. 321-328.
Kim, et al., Prediction of Binary Azeotrope Formation in Hydrocarbon Mixtures Using a Knowledge-Based Expert System, Korean J. Chem. Eng., 12:306-312, 1995.

(Continued)

*Primary Examiner* — Cephia D Toomer

(57) ABSTRACT

A process for determining the distillation characteristics of a liquid petroleum product that contains an azeotropic mixture of an oxygenated or nitrogen-containing component and at least one petroleum blending component.

12 Claims, 15 Drawing Sheets

(56) References Cited

U.S. PATENT DOCUMENTS

| | | |
|---|---|---|
| 8,465,560 B1 | 6/2013 | Wolf |
| 8,734,543 B2 | 5/2014 | Baustian |
| 8,870,983 B2 | 10/2014 | Baustian et al. |
| 8,876,924 B2 | 11/2014 | Torres-Ordonez et al. |
| 8,968,429 B2 | 3/2015 | Baustian et al. |
| 8,969,050 B2 | 3/2015 | Austin et al. |
| 9,217,737 B2 | 12/2015 | Boyd et al. |
| 9,359,568 B2 | 6/2016 | Baustian et al. |
| 9,388,353 B2 | 7/2016 | Torres-Ordonez et al. |
| 2006/0162243 A1 | 7/2006 | Wolf |
| 2009/0099401 A1 | 4/2009 | D'Amore et al. |
| 2009/0199464 A1 | 8/2009 | Wolf |
| 2009/0292512 A1 | 11/2009 | Wolf |
| 2010/0307053 A1 | 12/2010 | Kuberka et al. |
| 2011/0023354 A1 | 2/2011 | Wolf |
| 2011/0283604 A1 | 11/2011 | Foster et al. |
| 2012/0144902 A1 | 6/2012 | Torres-Ordonez et al. |
| 2012/0240454 A1 | 9/2012 | Boyd et al. |
| 2013/0180164 A1 | 7/2013 | Wolf |
| 2013/0227878 A1 | 9/2013 | Wolf et al. |
| 2013/0247450 A1 | 9/2013 | Wolf |
| 2013/0247453 A1 | 9/2013 | Baustian et al. |
| 2014/0005443 A1 | 1/2014 | D'Amore et al. |
| 2014/0109467 A1 | 4/2014 | Wolf |
| 2015/0007488 A1 | 1/2015 | Baustian et al. |
| 2015/0007490 A1 | 1/2015 | Torres-Ordonez et al. |
| 2015/0007491 A1 | 1/2015 | Baustian et al. |
| 2015/0128486 A1 | 5/2015 | Baustian et al. |
| 2015/0191686 A1 | 7/2015 | Austin et al. |

OTHER PUBLICATIONS

Petroleum Fractions Interface Specification, Open Interface Specification: Petroleum Fractions Interface, version 2, Aug. 2003.

Robbins, et al., "Petroleum, Composition," 1999-2014 Kirk-Othmer Encyclopedia of Chemical Technology, John Wiley & Sons, Inc.; DOI: 10.1002/0471238961.

Speight, "Petroleum Refinery Processes," 1999-2014 Kirk-Othmer Encyclopedia of Chemical Technology, John Wiley & Sons, Inc.; DOI: 10.1002/0471238961.

International Preliminary Report on Patentability dated Dec. 2, 2010 in corresponding PCT/US2009/044668.

Glindemann, et al., Role of azeotropy in characterization of complex hydrocarbon mixtures by true-boiling-point distillation, Fluid Phase Equilibria, 135:149-167, 1997.

Roekens, et al., Azeotropic Data for the Systems Formed by Representatives of the Homologous Series of Alkanes and Alcohols, J. Appl. Chem. Biotechnol. 26:595-610, 1976.

Lee, et al., Prediction of Azeotrope by Activity Coefficient Models without Parameters, J. Chinese Institute of Chemical Engineers 27:295-315, 1996.

Smith, et al., Improvements in the Measurement of Distillation Curves. 3. Application to Gasoline and Gasoline + Methanol Mixtures. Ind. Eng. Chem. Res. 46:297-309, 2007.

DeMenezes, et al., Addition of an azeotropic ETBE/ethanol mixture in eurosuper-type gasolines, Fuel 85:2567-2577, 2006.

International Search Report and Written Opinion of corresponding PCT/US2009/044668 dated Oct. 13, 2009.

\* cited by examiner

PROCESS FOR DETERMINING THE DISTILLATION CHARACTERISTICS OF A LIQUID PETROLEUM PRODUCT CONTAINING AN AZEOTROPIC MIXTURE

This application is a continuation-in-part of U.S. patent application Ser. No. 12/469,373, filed May 20, 2009, which claims benefit of U.S. Provisional Patent Application No. 61/055,284, filed May 22, 2008, each of which is incorporated herein by reference in its entirety. This application is a continuation-in-part of U.S. patent application Ser. No. 15/179469, filed Jun. 10, 2016, which is a continuation of U.S. patent application Ser. No. 14/497,682, filed Sep. 26, 2014, now U.S. Pat. No. 9,388,353, issued Jul. 12, 2016, which is a divisional of U.S. patent application Ser. No. 13/162,206, filed Jun. 16, 2011, now U.S. Pat. No. 8,876,924, issued Nov. 4, 2014, which claims benefit of U.S. Provisional Patent Application No. 61/355,222, filed Jun. 16, 2010, each of which is incorporated herein by reference in its entirety.

FIELD OF THE INVENTION

The present invention provides methods for determining the distillation characteristics of a petroleum product that contains an azeotropic mixture of an oxygenated or nitrogen-containing compound and at least one petroleum blending component.

BACKGROUND OF THE INVENTION

Distillation and Reid Vapor Pressure (RVP) properties of gasoline and diesel fuel influence vehicle performance such as cold start and warm-up, deposit-forming tendency, and emissions such as evaporative and engine-out exhaust. In fact, these volatility characteristics are subject to regulation by the United States Environmental Protection Agency (EPA) as well as state regulation. For example, certain states require fuels meet the American Society for Testing and Materials (ASTM) D4814 gasoline standard ("Standard Specification for Automotive Spark-Ignition Engine Fuel") and/or the ASTM D975 diesel standard ("Standard Specification for Diesel Fuel Oils"). Standards for fuels within much of Europe are generally set forth in European Standard EN228 ("Automotive Fuels—Unleaded Petrol—Requirements and Test Methods") and EN590 ("Diesel Fuel Testing"). In order to meet these standards, it would be highly desirable to develop a blending model for accurately predicting the distillation characteristics for petroleum products.

Mathematical models or mathematical relations may be used to characterize a petroleum product (e.g., fuel) utilizing physical properties and/or the environmental conditions such as temperature and pressure. A mathematical relation is the relationship between sets of variables or elements and may be expressed as an equation or graph. For example, the vapor pressure of a pure compound may be described using the Antoine equation:

$$\log P = A \frac{B}{T+C} \qquad \text{Equation 1}$$

where T is a particular temperature and A, B, and C are arithmetic constants known as Antoine coefficients. Antoine coefficients are available for numerous components including ethanol, isobutanol, benzene, n-pentane, cyclopentane, n-hexane, cyclohexane, toluene, and n-octane (see, e.g., Dean, Lange's Handbook of Chemistry, McGraw-Hill, Inc., 1999; NIST Chemistry WebBook). Mathematical models for blending are equations that describe the physical properties of a mixture of blending components based on the physical properties of each blending component and the amount of each blending component in the mixture (see, e.g., Cerdá, et al., Ind. Eng. Chem. Res. 55:7782-7800, 2016).

Mathematical relationships can be continuous mathematical functions. As an example, the expression $y = f(x)$ relates values of "y" to values of "x" by the operations defined by "f( )" The function, $f(x)$, includes the variable x and can include arithmetic constants and various mathematical operations such as multiplication, division, addition, subtraction, and transcendental operations such as logarithms or trigonometric functions. Values of x for which the function, $f(x)$, is defined are the "domain" of the function. The corresponding values of y are the "range" of the function (i.e., the range extends from the smallest to the largest values of y, not necessarily related to the smallest and largest values of x). Functions may also depend on more than one variable. For example, the expression $y = g(x, z)$ relates values of y to values of x and z by the operations defined by $g( )$. These functions may have more than two variables.

For mathematical blending models, a continuous function $y = g(x, z)$ can relate a physical property of a blend ("y") to the physical properties of the blending components ("x") and/or the amounts of the blending components ("z"). Given the values for x and z, the blend property can be predicted (i.e., calculated). In general, blending models are valid over certain values of x and z. For example, if z is the volume percent (vol %) of any particular component in a blend, it can only have values between 0% and 100%. Thus, the domain for z is 0% to 100% for the function $g(x, z)$. To establish mathematical relationships or blending models, the linear or ordinary least squares method (see, e.g., Numerical Recipes, Press, W. H., et al., University of Cambridge Press 1986, "General Linear Least Squares" pp. 509-520) may be used to determine coefficients for functions relating a physical property to linear combinations of the independent variables or a non-linear least squares method may be used for functions that are not linear in the coefficients (see, e.g., Numerical Recipes, Press, W, H., et al., University of Cambridge Press 1986, "Non-linear Models" pp. 521-528).

For blends consisting of only hydrocarbon components, blend properties are usually related to the component properties and their mole (or volume) fractions because the blends behave nearly "ideally" in the sense that molecular interactions between the constituent individual hydrocarbon compounds are similar to each other. However, the blend properties of a binary composition of a hydrocarbon compound plus an oxygenate or nitrogen-containing component may not be related to the component properties. Further, the azeotrope properties (e.g., boiling point and composition) of a binary mixture of an individual hydrocarbon compound plus oxygenate or nitrogen-containing component are only known for some individual hydrocarbon compounds.

Petroleum-based fuels such as gasoline and diesel fuel are obtained from crude petroleum utilizing various physical and chemical operations in a refinery. Crude petroleum is a mixture of hundreds if not thousands of individual hydrocarbon compounds and has a very wide boiling range, for example, 60° F. to more than 100° F. (Robbins, W. K. and Hsu, C. S., "Petroleum, Composition," 1999-2014 Kirk-Othmer Encyclopedia of Chemical Technology, John Wiley & Sons, Inc.; DOI: 10.1002/0471238961). Thus, although the refinery input stream can be highly variable, refining processes produce hydrocarbon streams that are blended together so that a consistent refinery product (e.g., gasoline or diesel fuel) is produced. These hydrocarbon streams are characterized by properties that are relevant to the refinery products, and standards such as ASTM D86 ("Standard Test Method for Distillation of Petroleum Products at Atmospheric Pressure") are used to characterize the properties of both the hydrocarbon streams and fuel products.

A key property of a fuel is its distillation characteristics, and distillation is used to separate crude petroleum or other streams into refinery streams with narrower boiling ranges that are composed of fewer individual hydrocarbon compounds as compared to the input stream. One reason to produce narrower boiling range streams is that fuel products such as gasoline and diesel fuel must have boiling ranges that include hydrocarbon compounds with proper combustion properties. In addition, producing narrower boiling range streams provides the various refinery processes with feed streams having the specific properties needed for effective operation (Speight, J. G. 2005 "Petroleum Refinery Processes," 1999-2014 Kirk-Othmer Encyclopedia of Chemical Technology, John Wiley & Sons, Inc.; DOI: 10.1002/0471238961). These feed streams that are blended together to produce the refinery products are often referred to as blending components. As noted above for refinery streams, blending components are composed of several to hundreds of individual hydrocarbon compounds. Refineries often produce several hydrocarbon blending components with variable properties and in various quantities that are blended together to produce a fuel that must meet technical standards such as ASTM D4814. As these hydrocarbon blending components can have variable properties and may be available in different quantities, it is a complex problem to blend fuels that meet technical standards using the volume of available blending components as well as optimizing the amount of fuel products produced.

As fuels must meet certain technical standards including distillation properties, it would be advantageous to be able to predict distillation properties of mixtures of blending components rather than using a trial and error method of mixing and testing many combinations of blending components. Refiners have developed mathematical models to calculate the distillation properties of blends of hydrocarbon components. However, fuel blends often include additional components such as oxygenates or nitrogen-containing components. It is know that some hydrocarbon-oxygenate fuel blends do not yield a final blend with distillation properties that are consistent with hydrocarbon only blending models. In particular, oxygenates such as alcohols can form binary low boiling azeotropes with individual hydrocarbons that boil at lower temperatures as compared to the individual alcohol and the individual hydrocarbon. Thus, predicting the distillation properties of alcohol-hydrocarbon blends can be challenging.

Distillation properties are often characterized by a distillation or boiling point curve (see, e.g., Perry's Chemical Engineers' Handbook, $8^{th}$ edition, Green, D. W. and Perry, R. H., Chapter 13 "Distillation," Section 13.10 "Petroleum and Complex Mixture Distillation, "McGraw-Hill, New York, 2008). A boiling point curve demonstrates the range of temperatures over which a compound boils and the corresponding amounts of the compound that have been recovered or evaporated at a particular temperature. ASTM D86 describes a standard test method for the distillation of petroleum products and the results of the distillation may be presented as percent hydrocarbon recovered or evaporated versus the corresponding temperature. Typically, temperatures of an initial boiling point (i.e., temperature of the first drop of condensate, "$T_{ibp}$"), 5%, 10%, 20%, 30, 40%, 50%, 60%, 70%, 80%, 90%, 95% condensate volumes recovered, and a final boiling point ("$T_{fbp}$") as well as the amounts of percent condensate recovered are recorded. Distillation data may be depicted by a smooth curve on a graph with temperature on the ordinate and volume percent on the abscissa (i.e., distillation curve).

The distillation curve or boiling curve represents the boiling properties of the combined individual hydrocarbons at various concentrations. The boiling curve may be considered to be a combination of distillation of several "narrow boiling fractions," each of which is composed of individual hydrocarbons that have boiling points relatively close together. Narrow boiling fractions may be composed of several individual hydrocarbons; however, the fractions behave more like a single hydrocarbon compound. The narrow boiling fractions are often referred to as "pseudo-components" because the fractions may be modeled mathematically like a single hydrocarbon compound. Pseudo-components may be defined by narrow temperature ranges rather than by fixed volume fractions (see, e.g., Table 13-30 in Perry's Chemical Engineers' Handbook, $8^{th}$ edition, Green, D. W. and Perry, R. H., Chapter 13 "Distillation," Section 13.10 "Petroleum and Complex Mixture Distillation," McGraw-Hill, New York, 2008).

Dividing a boiling curve into narrow boiling fractions by temperature or volume depends on the relative range of the boiling curve. For example, relatively smaller boiling ranges, $T_{fbp}$-$T_{ibp}$ less than about 350°, may be divided by 10 to 13 volume percent ("vol %") increments, whereas larger boiling ranges, $T_{fbp}$-$T_{ibp}$ greater that about 350°, may be divided into temperature increments, for example, of 10° F., 25° F., or 50° F. As an example, narrow boiling fractions representing a specific vol % may be associated with a temperature as follows: (i) a narrow fraction of 5 vol % is assigned to the initial boiling point, $T_{ibp}$; (ii) a narrow fraction of 10 vol % is assigned to $T_{10}$ (temperature corresponding to 10% volume recovered or evaporated); (iii) a narrow fraction of 10 vol % is assigned to $T_{20}$ (temperature corresponding to 20% volume recovered or evaporated); (iv) a narrow fraction of 10 vol % is assigned to $T_{30}$ (temperature corresponding to 30% volume recovered or evaporated); (v) a narrow fraction of 10 vol % is assigned to $T_{40}$ (temperature corresponding to 40% volume recovered or evaporated); (vi) a narrow fraction of 10 vol % is assigned to $T_{50}$ (temperature corresponding to 50% volume recovered or evaporated); (vii) a narrow fraction of 10 vol % is assigned to $T_{60}$ (temperature corresponding to 60% volume recovered or evaporated); (viii) a narrow fraction of 10 vol % is assigned to $T_{70}$ (temperature corresponding to 70% volume recovered or evaporated); (ix) a narrow fraction of 10 vol % is assigned to $T_{80}$ (temperature corresponding to 80% volume recovered or evaporated); (x) a narrow fraction of 10 vol % is assigned to $T_{90}$ (temperature corresponding to 90% volume recovered or evaporated); and (xi) a narrow fraction of 5 vol % is assigned to the final boiling point, $T_{fbp}$.

The present invention provides methods for determining the azeotrope properties of binary compositions of hydrocarbon compounds and oxygenate or nitrogen-containing compounds for unknown azeotrope combinations. The present invention also provides methods to generate distillation curves for blends of hydrocarbon blending components and oxygenates or nitrogen-containing compounds using these determined azeotrope properties. The present invention provides methods to calculate distillation properties of a hydrocarbon mixture when the proportions of the individual hydrocarbon compounds are unknown and the azeotropic properties of individual hydrocarbon compounds are unknown in a hydrocarbon-oxygenate mixture. As fuels such as gasoline and diesel can be mixtures of refinery hydrocarbon blending components, the methods of the present invention may be used to predict the distillation characteristics for petroleum products in order to produce gasoline and diesel fuel blends.

SUMMARY OF THE INVENTION

The present invention is directed to a process for determining the distillation characteristics of a petroleum product that contains an azeotropic mixture of an oxygenated or nitrogen-containing component and at least one petroleum blending component, comprising: (a) determining the mathematical relationship between the boiling points of hydrocarbons between specified minimum and maximum hydrocarbon boiling temperatures and the concentration of each such hydrocarbon in its binary azeotrope with the oxygenated or nitrogen-containing component (b) determining the mathematical relationship between the boiling points of the hydrocarbons and the boiling points of such binary azeotropes between the minimum and maximum hydrocarbon boiling temperatures; (c) dividing the boiling point curve of the combined at least one petroleum blending component between initial and final boiling points into narrow volume percent distillate fractions to thereby provide a defined distillation temperature for each such volume percent distillate fraction; (d) for each volume percent distillate fraction from step (c), (i) from the relationship from step (a), determining the total concentration of hydrocarbons in the distillate fraction; (ii) from the total concentration of hydrocarbons from step (d)(i) and starting from the lowest volume percent distillate fraction, determining the amounts of the azeotropic mixture and of the oxygenated or nitrogen-containing component in the distillate fraction for each such volume percent distillate fraction; and (iii) from the relationship from step (b), determining the boiling point of the azeotropic mixture that corresponds to each such volume percent distillate fraction; and (e) for each volume percent distillate fraction correlating the amount of the azeotropic mixture in the distillate fraction from step (d)(ii) with the boiling point from step (d)(iii), and combining such correlations to thereby determine the distillation characteristics of the liquid petroleum product.

The present invention is directed to a process for determining the distillation characteristics of a liquid petroleum product that contains an azeotropic mixture of an oxygenated or nitrogen-containing component and at least one petroleum blending component comprising (a) defining a relationship between the boiling points of hydrocarbons of the liquid petroleum product and the concentration of each such hydrocarbon in an azeotrope with the oxygenated or nitrogen-containing component; (b) defining a relationship between the boiling points of the hydrocarbons and the boiling points of the azeotropes; (c) generating a boiling point curve of narrow volume percent distillate fractions and distillation temperature for each such volume percent distillate fraction; (d) for each volume percent distillate fraction from step (c): (i) determining the total concentration of hydrocarbons in the distillate fraction; (ii) determining the amounts of the azeotropic mixture and of the oxygenated or nitrogen-containing component in each such volume percent distillate fraction and (iii) determining the boiling point of the azeotropic mixture that corresponds to each such volume percent; and (e) correlating for each volume percent distillate fraction the amount of the azeotropic mixture in the distillate fraction from step (d)(ii) with the boiling point from step (d)(iii), and combining such correlations to thereby determine the distillation characteristics of the liquid petroleum product.

In one embodiment of the processes of the present invention, the oxygenated component is an alcohol, ester, ketone, ether, ester alcohol, keto-alcohol, ether alcohol, aldehyde, ether aldehyde, or aldehyde alcohol. In some embodiments, the oxygenated component is at least one alcohol. In some embodiments, the oxygenated component is ethanol. In some embodiments, the oxygenated component is an isomer of butanol. In some embodiments, the isomer of butanol is 1-butanol, 2-butanol, isobutanol, tert-butanol. In some embodiments, the oxygenated component is a mixture of one or more oxygenates. In some embodiments, the oxygenated component is a mixture of one or more alcohols. In some embodiments, the nitrogen containing component is an amine, amide, nitrile, nitro ester, nitrate ester, nitrite ester, cyclic nitrogen compound, amino alcohol, ether amine, or poly amine. In some embodiments, the nitrogen containing component is a mixture of one or more nitrogen containing components. In some embodiments, the nitrogen containing component is a mixture of one or more nitrogen containing components and one or more oxygenated components. In some embodiments, the liquid petroleum product is a gasoline.

DESCRIPTION OF THE INVENTION

Figure 1:
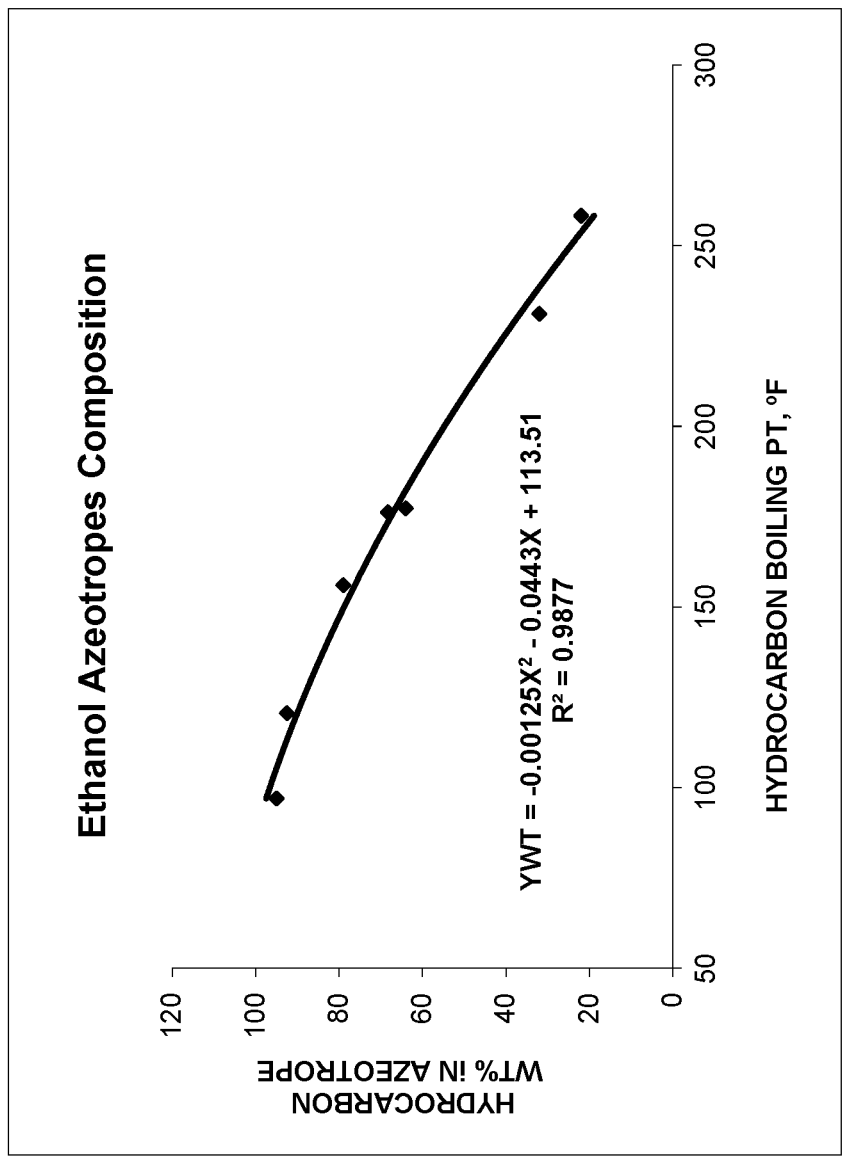
FIG. 1 illustrates a relationship between a hydrocarbon composition of an ethanol azeotrope and a domain within specified maximum and minimum boiling temperatures of the individual hydrocarbon component.

In order to further define this invention, the following terms and definitions are herein provided.

The term "fuel" as used herein, refers to any material that can be used to generate energy to produce mechanical work in a controlled manner. Examples of fuels include, but are not limited to, biofuels (i.e., fuels which are in some way derived from biomass), gasoline, gasoline subgrades, diesel and jet fuel. It is understood that the specific components and allowances of suitable fuels can vary based on seasonal and regional guidelines.

The term "gasoline" as used herein, generally refers to a volatile mixture of liquid hydrocarbons that can optionally contain small amounts of additives. This term includes, but is not limited to, conventional gasoline, oxygenated gasoline, reformulated gasoline, biogasoline (e.g., gasoline which in some way is biologically derived from biomass), Fischer-Tropsch gasoline, and mixtures thereof. Additionally, the term "gasoline" may include a gasoline blend, gasoline blends, blended gasoline, a gasoline blend stock, gasoline blend stocks, and mixtures thereof. It is understood that the specific components and allowances of gasolines can vary based on seasonal and regional guidelines. The specifications for gasolines set forth in ASTM D4814 vary based on a number of parameters affecting volatility and combustion such as weather, season, geographic location, and altitude.

The terms "gasoline blend" and "blended gasoline" as used herein, refer to a mixture containing at least a gasoline and/or gasoline subgrade and/or mixtures of one or more refinery gasoline blending components (e.g., alkylate, reformate, FCC naphthas) and optionally, one or more alcohols. A gasoline blend includes, but is not limited to, an unleaded gasoline suitable for combustion in an automotive engine.

The terms "fuel blend" and "blended fuel" as used herein, refer to any material that can be used to generate energy to produce mechanical work in a controlled manner and that contains one or more alcohols. Examples of fuel blends include, but are not limited to, gasoline blends, diesel blends, and jet fuel blends. It is understood that the specific components and allowances of fuel blends can vary based on seasonal (e.g., winter or summer grade) and regional guidelines and technical standards, and can be based, at least in part, on the allowances, guidelines, and/or standards for fuels that are not blended with alcohols or for ethanol blended fuels.

The term "naphtha" refers to a number of different flammable liquid mixtures of hydrocarbons, for example, a distillation product from petroleum or coal tar boiling in a certain range and containing certain hydrocarbons. Naphtha can be, for example, "light naphtha" or "heavy naphtha." Heavy naphtha contains denser types of napthas and are typically richer in napthenes and aromatics. Light naphtha contains less dense types of napthas and has a higher paraffin content. Light naphtha can contain pentane, butane, or any mixtures thereof. Naphtha can also be, for example, "upgraded naphtha." Upgraded naphtha is a naphtha stream that has been processed by one or more octane upgrading units.

The term "crude oil" or "crude petroleum" refers to a mixture of naturally occurring hydrocarbons that is refined into diesel, gasoline, heating oil, jet fuel, kerosene, or other petrochemical products. Crude oils are named according to their contents and origins, and classified according to their per unit weight (specific gravity).

The term "vapor pressure" as used herein, refers to the pressure of a vapor in thermodynamic equilibrium with its condensed phases in a closed system. For a fuel at high temperatures, it is necessary to maintain a lower vapor pressure to reduce the possibility of vapor lock, carbon canister overloading, and evaporative emissions; and at lower temperatures, a higher vapor pressure is needed for good starting and warm-up performance.

The terms "Reid Vapor Pressure" and "RVP" as used herein, refers to the absolute vapor pressure exerted by a liquid at 100° F. (37.8° C.) as determined by the test method ASTM D323 ("Standard Test Method for Vapor Pressure of Petroleum Products," the Reid Method).

A "distillation column" separates the components of crude oil based on differences in the volatilities of the components of the crude oil in a boiling liquid mixture. A "distillate" contains the products of distillation. A distillate can be a "light distillate," "middle distillate," or a "heavy distillate." A light distillate fractions near the top of the distillation column and has a lower boiling point than the lower fractions of the distillation column. An example of a light distillate is a light naphtha. A middle distillate fractions near the middle of the distillation column and has a lower boiling point than the lower fractions of the distillation column. Examples of a middle distillate include kerosene and diesel. A heavy distillate is a fraction near the bottom of the distillation column having a higher boiling point than the upper fractions of the distillation column. Examples of a heavy distillate include heavy fuel oil, lubricating oils, wax, and asphalt.

Distillation columns may also be used to separate raw product streams from a conversion process (e.g., hydrocracker unit) into two or more streams with narrower boiling ranges as compared to the unit's raw product. For example, the raw product of a hydrocracker unit may be separated into a naphtha (e.g., gasoline boiling range) stream and a distillate (e.g., diesel fuel boiling range) stream.

"Normal boiling point" is the temperature at which a liquid boils at one atmosphere (atm) pressure or at which the vapor pressure of a liquid equals one atm.

An "azeotrope" is a mixture of liquids that exhibits the same concentration in the vapor phase and the liquid phase and has a constant boiling point.

A "hydrotreater unit" can perform a number of diverse processes including, for example, the conversion of benzene to cyclohexane, aromatics to naphthas, and the reduction of sulfur and nitrogen levels. A hydrotreater unit may also include desulfurization.

A "hydrocracker unit" is an apparatus which breaks down heavy hydrocarbons typically using moderate temperature, elevated pressure, and a bifunctional catalyst capable of rearranging and breaking hydrocarbon chains and adding hydrogen to aromatics and olefins to produce naphthenes and alkanes. Hydrogen is consumed during hydrocracking.

Hydrocracking results in the purification of the input stream of sulfur and nitrogen heteroatoms.

A "hydrosulfurization unit" or " hydrodesulfurization unit" is an apparatus used to remove sulfur from petroleum products such as gasoline, diesel fuels, and jet fuel utilizing a catalytic chemical process at high temperature and pressure in the presence of hydrogen. By removing sulfur, sulfur dioxide emissions generated by vehicles, aircraft, ships, and the like are reduced. In addition, sulfur can have a negative effect on catalysts (e.g., molybdenum disulfide, ruthenium disulfide) used in catalytic reforming units.

The term "oxygenate" as used herein refers to a compound containing only carbon, hydrogen, and one or more oxygen atoms. For example, oxygenates may be alcohols, ketones, esters, aldehydes, carboxylic acids, ethers, ether alcohols, ketone alcohol, poly alcohols, or combinations thereof. Alcohols may include ethanol, isomers of propanol, isomers of butanol, and combinations thereof. Isomers of butanol include 1-butanol, 2-butanol, isobutanol, and tert-butanol. In some instances, oxygenates may be derived from biomass such as corn, sugar cane, wheat, rye, barley, switchgrass, cellulosic, or lignocellulosic material.

The terms "renewable component" as used herein refers to a component that is not derived from petroleum or petroleum products.

Gasolines and diesel fuels are well known in the art and generally contain as a primary component a mixture of hydrocarbons having different boiling points and typically boil at atmospheric pressure at temperatures in the range of about 79° F. to about 437° F. for gasolines and in the range of about 360° F. to about 710° F. for diesel fuels. These ranges are approximate and can vary depending upon the actual mixture of hydrocarbons, additives or other compounds, and environmental conditions. Oxygenated gasolines and oxygenated diesel fuels are blends of either a gasoline blend stock or a diesel fuel blend stock and one or more oxygenates. Examples of hydrocarbons that may be employed in as refinery streams are shown in Table 1.

TABLE 1

| Stream Name | Approximate Distillation, ° F. | | | Major Chemical types |
|---|---|---|---|---|
| | T10 | T50 | T90 | |
| Isomerate | 116 | 130 | 160 | branched C5-C6 paraffins |
| Light virgin naphtha | 95 | 130 | 180 | C5-C8 paraffins, cycloparaffins, olefins, aromatics |
| Light straight run naphtha | 95 | 130 | 180 | C5-C8 paraffins, cycloparaffins, olefins, aromatics |
| Light catalytically cracked naphtha | 110 | 140 | 250 | C5-C8 paraffins, cycloparaffins, olefins, aromatics |
| Light hydrocracked naphtha | 110 | 130 | 175 | C5-C8 paraffins, cycloparaffins, aromatics |
| Light hydrotreated coker naphtha | 115 | 140 | 200 | C5-C8 paraffins, cycloparaffins, aromatics |
| Light hydrotreated naphtha | 115 | 140 | 200 | C5-C8 paraffins, cycloparaffins, aromatics |
| Light alkylate | 165 | 215 | 230 | C6-C9 branched paraffins |
| Light reformate | 150 | 190 | 240 | C7-C8 aromatics |
| Raffinate | 150 | 180 | 240 | C6-C9 paraffins, cycloparaffins |

Gasoline and diesel fuel blend stocks may be produced from a single component, such as a product from a refinery alkylation unit (e.g., combines isobutane and an alkene to produce alkylate) or other refinery streams. However, gasoline and diesel fuel blend stocks are more commonly blended using more than one component. For example, gasoline and diesel fuel blend stocks may include a few components (e.g., three or four) or may include many components (e.g., twelve or more). Gasolines, diesel fuels, gasoline blend stocks, and diesel fuel blend stocks may optionally include other chemicals or additives. For example, additives or other chemicals may be added to adjust properties of a gasoline or diesel fuel to meet regulatory requirements, to add or enhance desirable properties, to reduce undesirable detrimental effects, to adjust performance characteristics, and/or to modify the characteristics of the gasoline or diesel fuel. Examples of such chemicals or additives include detergents, antioxidants, stability enhancers, demulsifiers, corrosion inhibitors, metal deactivators, lubricity improvers, friction modifiers, cold flow improvers, and others. More than one additive or chemical may be used. Useful additives and chemicals are described in U.S. Pat. No. 5,782,937; U.S. Pat. No. 6,083,228; U.S. Pat. No. 5,755,833; U.S. Pat. No. 5,858,028; U.S. Pat. No. 5,997,592; U.S. Pat. No. 6,248,142; U.S. Pat. No. 6,280,488; and U.S. Pat. No. 6,277,159, all of which are incorporated herein by reference. Gasolines, diesel fuels, gasoline blend stocks, or diesel fuel blend stocks may also contain solvent or carrier solutions which are often used to deliver additives into a fuel. Examples of such solvents or carrier solutions include, but are not limited to, mineral oil, alcohols, carboxylic acids, synthetic oils, and numerous other which are known in the art. In addition, components of gasoline and diesel fuel blend stocks may include renewable components.

Gasoline and diesel fuel blend stocks suitable for use in the methods of this invention are typically blend stocks used for producing gasolines and diesel fuels for spark or compression ignition engines or in other engines which combust gasoline or diesel fuel. Suitable gasoline blend stocks include blend stocks for gasolines meeting the ASTM D4814 standard and blend stocks for reformulated gasoline. Suitable gasoline blend stocks also include blend stocks having low sulfur content which may be desired to meet regulatory requirements, for example, sulfur content less than about 150 parts per million, less than about 100 parts per million, less than about 80 parts per million, less than about 50 parts per million, or less than about 30 parts per million. Such suitable gasoline blend stocks also include blend stocks having low aromatics content which may be desirable to meet regulatory requirements. For example, benzene in gasoline blend stocks may be less than about 6000 parts per million or less than about 5000 parts per million; or total aromatic species in gasoline blend stocks may be less than about 35 volume percent or less than about 25 volume percent.

Suitable diesel fuel blend stocks include blend stocks for diesel fuels meeting the ASTM D975 standard. Suitable diesel fuel blend stocks include light middle distillate or kerosene, heavy middle distillate, light catalytic cracker cycle oil, coke still distillate, light and heavy hydrocracker distillates, and hydrotreater distillates. Also, such diesel fuel blend stocks may be blended together as feed to a hydrosulfurization unit to reduce sulfur level as may be required by regulations. The product stream from such a hydrosulfurization unit may then be used as a suitable diesel fuel component to blend with an oxygenate.

An oxygenate such as ethanol may be blended with gasoline or diesel fuel blending stocks at any point within the fuel distribution chain. For example, one or more blending stocks and one or more oxygenates may be combined at a refinery, or one or more blending stocks may be combined at a refinery and then transported to a terminal where one or more oxygenates may be blended with the gasoline blend stock or diesel fuel blend stock.

In order to produce gasoline and diesel fuel with the most economic blend in view of the operating constraints of a refinery, refiners utilize models to predict the properties of the final blends based upon the properties of available blending stocks. Therefore, a model that accurately predicts the properties of a blend is an important tool. For example, models predicting distillation characteristics are important because the gasoline distillation points $T_{10}$, $T_{50}$, and $T_{90}$ and the diesel fuel distillation point $T_{90}$ have specifications depending on the season and geographic location (distillation point $T_{10}$ represents the temperature that 10% gasoline is evaporated; $T_{50}$ represents the temperature that 50% gasoline is evaporated; and $T_{90}$ represents the temperature that 90% gasoline or diesel fuel is evaporated).

The blending models for conventional gasoline and diesel fuel can be relatively straightforward because the hydrocarbon blending stocks behave nearly ideally, and the vapor pressure of mixtures follows Raoults' Law or does so with minor modifications. However, the vapor pressure of oxygenated fuels, particularly oxygenates such as alcohols (e.g., ethanol, propanol, and butanol), esters, ketones, ethers, ester alcohols, keto-alcohols, ether alcohols, aldehydes, ether aldehydes, and aldehyde alcohols are non-ideal and therefore, the blend models for such oxygenated fuels are not as straightforward. Thus, it would be highly desirable to develop a blending model for accurately predicting the distillation characteristics for petroleum products comprising oxygenates (i.e., azeotropic mixtures).

Nitrogen-containing compounds such as amines, amides, nitriles, and nitro esters are also known to form non-ideal mixtures with hydrocarbons and therefore, these blend models are also not as straightforward. In addition, bioderived blending components containing nitrogen are being produced from biomass such as nitriles derived from vegetable oils (described as "high energy biodiesel," HEBD). Future bioderived blending components may contain significant amounts of nitrogen because of their biological origin. A blend model for these nitrogen-containing compounds would be advantageous to evaluate their impact on blend distillation characteristics.

For the purpose of illustration only, the methods of this invention will be exemplified using a gasoline and an oxygenated component (e.g., ethanol, isobutanol) blend. As an example, the first two steps (e.g., steps a and b) of a multi-step method of the present invention involve determining or defining relationships between specified minimum and maximum boiling temperatures. The specific minimum and maximum boiling temperatures depend on the identity of the specific oxygenated component involved. For example, the specified minimum and maximum temperatures for hydrocarbons that form azeotropes with ethanol are 90° F. and 275° F., respectively. These temperatures were determined from data in Table 2 that provides individual hydrocarbon boiling points for hydrocarbons that form binary azeotropes with ethanol (see, e.g., Handbook of Chemistry and Physics, 67$^{th}$ edition, CRC Press, 1986, page D-15). The domain is slightly extrapolated to a lower temperature (i.e., 90° F. compared to 96.98° F.) to accommodate possible azeotropes with greater than 95% hydrocarbon, and higher temperature (i.e., 275° F. compared to 258.26° F.) to accommodate possible azeotropes with less than 22% hydrocarbon and where the azeotrope boiling point reaches the boiling point of pure ethanol, 173.3° F.

The first relationship, step (a), is between (i) the boiling points of the individual hydrocarbons that boil between the specified minimum and maximum individual hydrocarbon boiling temperatures and (ii) the concentration of each individual hydrocarbon in its binary azeotrope with an alcohol component (e.g., ethanol, propanol, butanol, or mixtures thereof). The second relationship, step (b), is between (i) the boiling points of the individual hydrocarbons and (ii) the boiling points of the binary azeotropes.

Individual hydrocarbons that form azeotropes with ethanol are, for example, n-pentane, cyclopentane, n-hexane, cyclohexane, benzene, toluene, and n-octane. The boiling points of the individual hydrocarbons, the boiling points of binary azeotropes with ethanol, both at atmospheric pressure, and the concentrations of the hydrocarbons in the azeotropes are presented in Table 2. The term "zeotrope" in Table 2 indicates that no azeotrope was formed, and wt % is the weight percent of the hydrocarbon in the azeotrope.

TABLE 2

| Hydrocarbon | Hydrocarbon Boiling Pt. (° F.) | Azeotrope with Isobutanol | | Azeotrope with n-butanol | | Azeotrope with 2-butanol | | Azeotrope with t-butanol | | Azeotrope with ethanol | |
|---|---|---|---|---|---|---|---|---|---|---|---|
| | | B. Pt. (° F.) | wt % | B. Pt. (° F.) | wt % | B. Pt. (° F.) | wt % | B. Pt. (° F) | wt % | B. Pt. (° F.) | wt % |
| n-pentane | 96.98 | | | | | | | | | 93.74 | 95 |
| cyclopentane | 97.07 | | | | | | | | | 112.46 | 92.5 |
| n-hexane | 156.02 | 154.94 | 97.5 | 154.76 | 96.8 | | | 146.66 | 78 | 137.62 | 79 |
| methyl cyclopentane | 161.6 | 159.8 | 95 | | | 157.46 | 88.5 | 151.88 | 74 | | |
| benzene | 176.18 | 174.74 | 92.6 | zeotrope | | 173.3 | 84.6 | 165.11 | 63.4 | 154.22 | 68.3 |
| cyclohexane | 177.35 | 172.94 | 86 | 175.64 | 90.5 | 168.8 | 82 | 160.16 | 65.8 | 148.64 | 70.8 |
| cyclohexene | 180.86 | 176.9 | 85.8 | 179.6 | 95 | | | | | | |
| n-heptane | 209.21 | 195.44 | 73 | 200.93 | 82 | 190.58 | 63.3 | 172.4 | 38 | | |
| 2,2,4-trimethyl pentane | 210.74 | 197.6 | 73 | | | 190.4 | 66.2 | | | | |
| methyl cyclohexane | 213.44 | 198.68 | 68 | 203.54 | 80 | 193.46 | 61.8 | 173.84 | 34 | | |
| 2,5-dimethyl hexane | 228.56 | 209.66 | 58 | | | | | 178.7 | 23 | | |
| toluene | 231.26 | 214.16 | 55 | 221.9 | 72.2 | 203.54 | 45 | zeotrope | | 170.06 | 32 |
| cis-1,3-dimethyl cyclohexane | 249.26 | 215.96 | 44 | | | | | | | | |
| n-octane | 258.35 | | | 227.21 | 54.8 | | | | | 170.6 | 22 |
| ethyl benzene | 277.07 | 224.96 | 20 | 240.53 | 34.9 | | | | | zeotrope | |

TABLE 2-continued

| Hydrocarbon | Hydrocarbon Boiling Pt. (° F.) | Azeotrope with Isobutanol | | Azeotrope with n-butanol | | Azeotrope with 2-butanol | | Azeotrope with t-butanol | | Azeotrope with ethanol | |
|---|---|---|---|---|---|---|---|---|---|---|---|
| | | B. Pt. (° F.) | wt % | B. Pt. (° F.) | wt % | B. Pt. (° F.) | wt % | B. Pt. (° F) | wt % | B. Pt. (° F.) | wt % |
| p-xylene | 281.12 | 224.78 | 11.4 | 240.26 | 32 | | | zeotrope | | zeotrope | |
| m-xylene | 282.2 | | | 241.7 | 28.5 | | | | | | |
| o-xylene | 290.48 | | | 242.24 | 25 | | | | | | |
| n-nonane | 303.26 | | | 240.62 | 28.5 | | | | | | |

Using the data in Table 2, the first relationship between the hydrocarbon composition of the azeotrope that is a continuous, monotonic function of the boiling temperature of the individual hydrocarbon and a domain within specified maximum and minimum boiling temperatures of the individual hydrocarbons is determined. The quadratic function of Equation 2 provides an example of a mathematical relationship between the hydrocarbon composition of an ethanol azeotrope and the individual hydrocarbon boiling point:

$$ywt = a_0 + a_1 x + a_2 x^2 \qquad \text{Equation 2}$$

where ywt is the percent of hydrocarbon in the azeotrope, x is the boiling temperature of the individual hydrocarbon, and $a_0$, $a_1$, and $a_2$ are coefficients of the equation. The coefficients of Equation 2 were determined by the ordinary least squares method with the azeotrope hydrocarbon weight percent as the dependent variable and the boiling point of the individual hydrocarbon and its square as the independent variables (i.e., data in Table 2). A continuous function is needed to allow interpolation of unknown azeotrope hydrocarbon compositions between compositions of known azeotropes. Additionally, a monotonic function is needed to avoid ambiguity, for example, more than one possible azeotrope composition for a specific hydrocarbon boiling point.

The domain of this function, that is, values of x that are applicable is established by the physical constraint that the range ywt is between 0% and 100%. An adjustable parameter may be employed in this step to account for any hydrocarbons that do not form azeotropes with the oxygenate, as evidenced by differences between the observed boiling point curve and the boiling point curve calculated as described below. For example, if only 90% of the individual hydrocarbons in the domain of x form azeotropes, ywt is multiplied by 0.90. The adjustable parameter may be determined by comparison of observed and calculated distillation curves. However, no such adjustment was necessary in these examples.

FIG. 1 illustrates the relationship for an ethanol azeotrope. The domain of the boiling temperature of the hydrocarbon variable is 90° F. to 275° F. inclusive (x-axis). The coefficients are $a_0$ is 113.51, $a_1$ is −0.0443, and $a_2$ is −0.00125, and the $R^2$ value is 0.9877 as determined by the ordinary least squares method. At the domain value of 90° F., the value of ywt is $113.51 - 0.0443 * 90 - 0.0012475 * 90^2 = 99.4\%$ and at 275° F., ywt is $113.51 - 0.0443 * 275 - 0.001247 * 275^2 = 7.0\%$. The domain thus gives compositions with hydrocarbon contents between 0 and 100%.

The second relationship, step (b), between the boiling point of the azeotrope that is a continuous, monotonic function of the boiling temperature of the individual hydrocarbon and a domain between specified maximum and minimum boiling temperatures of the individual hydrocarbon is determined. The quadratic function of Equation 3 provides an example of a mathematical relationship between the boiling point of an ethanol azeotrope and the individual hydrocarbon boiling point:

$$ybp = b_0 + b_1 x + b_2 x^2 \qquad \text{Equation 3}$$

where ybp is the boiling temperature of the azeotrope, x is the boiling temperature of the hydrocarbon and $b_0$, $b_1$, and $b_2$ are coefficients of the equation. The relationship was determined by a standard least squares regression with the azeotrope boiling point as the dependent variable and the boiling point of the individual hydrocarbon and its square as the independent variables (i.e., data in Table 2). A continuous function is needed to allow interpolation of azeotrope boiling points between boiling points of known azeotropes. Additionally, a monotonic function is needed to avoid ambiguity, for example, more than one possible azeotrope boiling point for a specific hydrocarbon boiling point.

Figure 2:
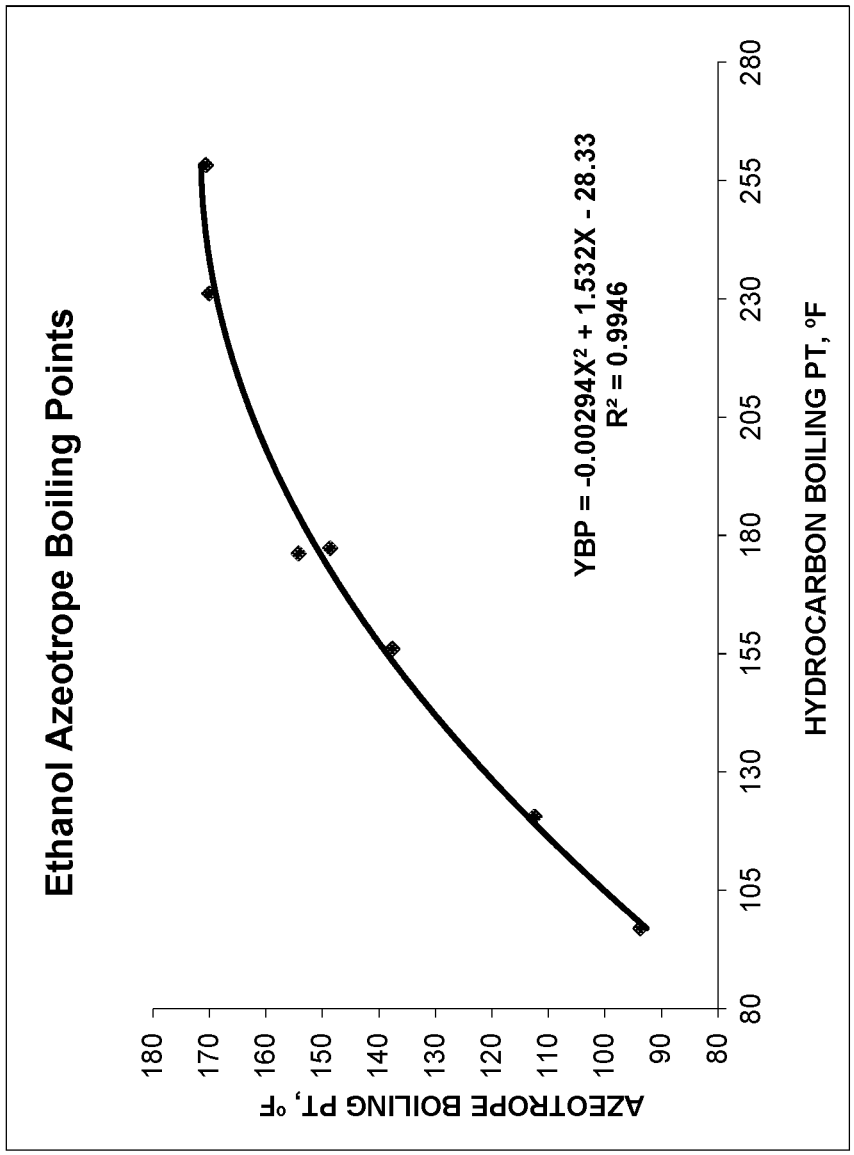
FIG. 2 illustrates a relationship between the boiling point of an ethanol azeotrope and a domain between specified maximum and minimum boiling temperatures of the individual hydrocarbon component.

FIG. 2 illustrates the second relationship for an ethanol azeotrope. The domain of the boiling temperature of hydrocarbon variable is 90° F. to 275° F. inclusive (x-axis). The coefficients are $b_0$ is −28.33, $b_1$ is 1.532, and $b_2$ is −0.00294, and the $R^2$ value is 0.9946 and was determined by the ordinary least squares method. The maximum and minimum values of x, the domain, for this function is 90° F. and 275° F. Also, the maximum value is $-28.33 + 1.53 * 275 - 0.00294 * 275^2 = 170.9$ which is close to the boiling point of the oxygenate, pure ethanol, which is 173.3° F. Thus, the domain for the first and second relationships is consistent with physical constraints on low boiling azeotropes: the hydrocarbon composition is between 0% and 100% and the maximum azeotrope boiling point is no higher than the oxygenate which is the lower boiling component of the azeotrope.

Petroleum blending components and combinations thereof are complex mixtures of hydrocarbons. The boiling curve of petroleum blending components and combinations are generally described by temperature vs vol % distilled and may be determined by various methods including the standard method ASTM D86. As an example, a boiling curve may be divided into narrow boiling ranges at volume intervals to represent hydrocarbon species in the complex mixture, step (c). For the hydrocarbon component described in Table 3, a narrow fraction consisting of the first 5 vol % is assigned a boiling point of 95.9° F.; a second narrow fraction of 10 vol % is assigned a boiling point of 123.3° F.; a third narrow fraction of 10 vol % is assigned a boiling point of 134.6° F., a fourth narrow fraction of 10 vol % is assigned a boiling point of 147.8° F., a fifth narrow fraction of 10 vol % is assigned a boiling point of 163.2° F., a sixth narrow fraction of 10 vol % is assigned a boiling point of 184.9° F., a seventh narrow fraction of 10 vol % is assigned a boiling point of 214.7° F., an eight narrow fraction of 10 vol % is assigned a boiling point of 260.7° F., a ninth narrow fraction of 10 vol % is assigned a boiling point of 322.7° F., a tenth narrow fraction of 10 vol % is assigned a boiling point of 348.8° F., and an eleventh narrow fraction of 5 vol % is assigned a boiling point of 412° F.

TABLE 3

| | Hydrocarbon Blending Component | |
|---|---|---|
| Narrow Fraction | Vol % Distilled | Temperature, ° F. |
| 1 | Initial Boiling Point | 95.9 |
| 2 | 10 | 123.3 |
| 3 | 20 | 134.6 |
| 4 | 30 | 147.8 |
| 5 | 40 | 163.2 |
| 6 | 50 | 184.9 |
| 7 | 60 | 214.7 |
| 8 | 70 | 260.7 |
| 9 | 80 | 322.7 |
| 10 | 90 | 348.8 |
| 11 | Final Boiling Point | 412 |

Figure 3:
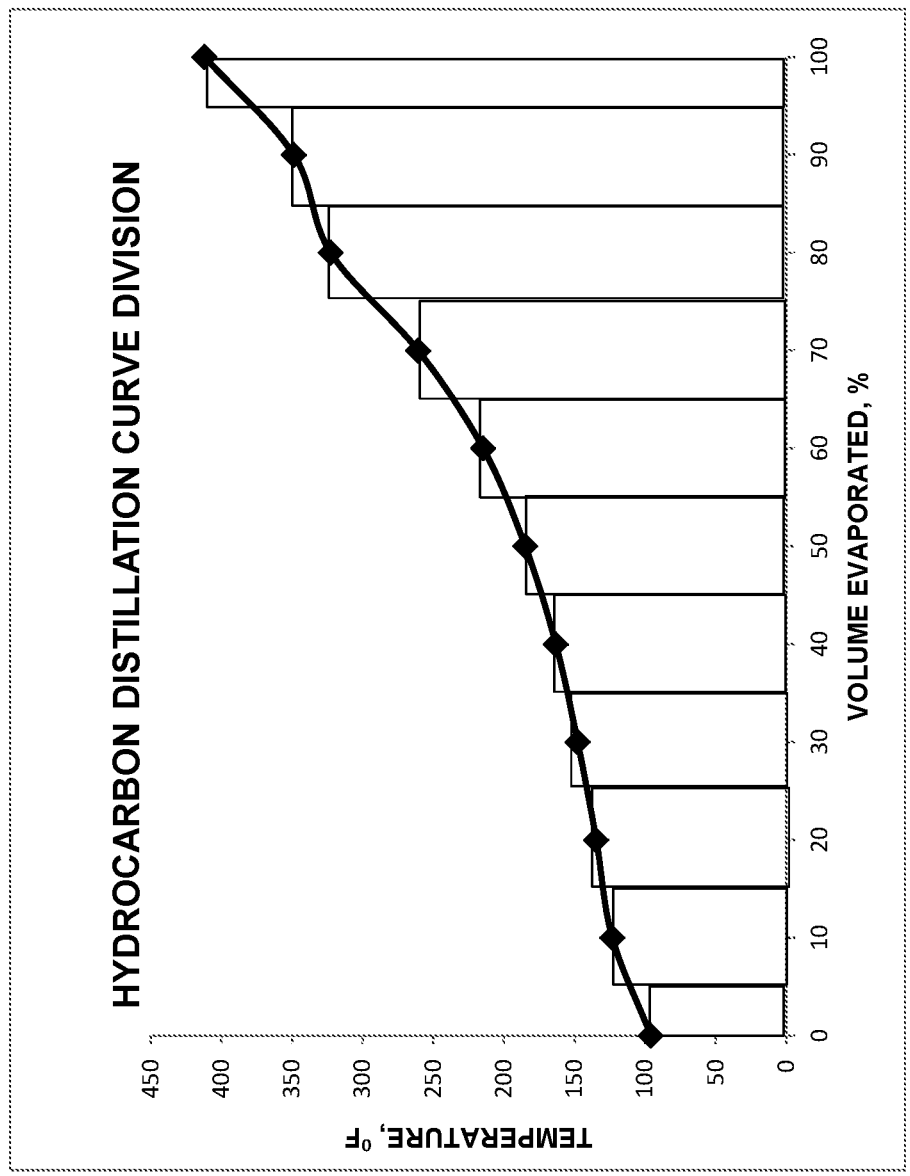
FIG. 3 illustrates a boiling curve divided into narrow boiling ranges at volume intervals (i.e., narrow boiling fractions) to represent hydrocarbon species in the complex mixture.

The narrow fractions with boiling points between 90° F. and 275° F. then represent hydrocarbons that may form azeotropes with ethanol. The minimum and maximum limits of azeotrope formation are the domain in which the mathematical correlations are valid (i.e., monotonic and continuous within reasonable extrapolation and interpolation of the known azeotrope data). FIG. 3 illustrates the process graphically, and the data are shown in columns 1 and 2 of Table 4.

TABLE 4

| 1 Boiling point (° F.) | 2 Narrow fraction volume | 3 90.5% Hydrocarbon of blend | 4 Ethanol in azeotrope of fraction | 5 Cumulative ethanol in blend | 6 Total azeotrope | 7 Hydrocarbon remain | 8 Boiling point, azeotrope or hydrocarbon |
|---|---|---|---|---|---|---|---|
| 95.9 | 5 | 4.525 | 0.102 | 0.102 | 4.627 | 0 | 91.6 |
| 123.3 | 10 | 9.05 | 1.108 | 1.210 | 10.158 | 0 | 115.9 |
| 134.6 | 10 | 9.05 | 1.603 | 2.813 | 10.653 | 0 | 124.7 |
| 147.8 | 10 | 9.05 | 2.302 | 5.115 | 11.352 | 0 | 134.0 |
| 163.2 | 10 | 9.05 | 3.336 | 8.451 | 12.386 | 0 | 143.5 |
| 184.9 | 10 | 9.05 | 1.049 | 9.5 | 2.812 | 7.287 | 154.6, 184.9 |
| 214.7 | 10 | 9.05 | 0 | 0 | 0 | 9.05 | 214.7 |
| 260.7 | 10 | 9.05 | 0 | 0 | 0 | 9.05 | 260.7 |
| 322.7 | 10 | 9.05 | 0 | 0 | 0 | 9.05 | 322.7 |
| 348.8 | 10 | 9.05 | 0 | 0 | 0 | 9.05 | 348.8 |
| 412 | 5 | 4.525 | 0 | 0 | 0 | 4.525 | 412 |

The boiling curve of petroleum blending components and their combinations may also be determined using alternate boiling curve data such as true boiling point (TBP) as described in ASTM D285 ("Method of Test for Distillation of Crude Petroleum") or simulated distillation as described in ASTM D2892 ("Standard Test Method for Distillation of Crude Petroleum"). In addition, the data may be converted, for example, by converting ASTM D86 data to TBP data utilizing methods known to those skilled in the art.

The amount of hydrocarbon in each fraction that forms an azeotrope with the oxygen or nitrogen compound in the final blend may be determined, step (d). As an example, the amount of hydrocarbon in a blend of 90.5% petroleum blending component and 9.5% ethanol was determined. These blends are often referred to as E1i) because 10% denatured ethanol is added to 90% hydrocarbon. Denatured ethanol historically was 95% ethanol and 5% hydrocarbon denaturant. The distillation data for the petroleum blending component of this blend is shown in Table 2.

The amount of hydrocarbon in each fraction available to form an azeotrope is 90.5% of the narrow fraction as shown in column 3 ("90.5% Hydrocarbon of blend") of Table 4 which was calculated by multiplying the narrow fraction volume by 0.905. The maximum volume of ethanol that can combine with a particular narrow fraction is given by its boiling point (i.e., similar to an individual hydrocarbon) and the relationship determined by step (a) (i.e., Equation 2). The maximum volume of ethanol may be determined, for example, by a simple addition of volumes within each narrow fraction:

$$V_A = V_{HC} + V_{Et} \quad \text{Equation 4}$$

where $V_A$ is the volume of azeotrope, $V_{HC}$ is the volume of hydrocarbon fraction of the azeotrope, and $V_{Et}$ is the volume of the ethanol fraction of the azeotrope. Using Equation 2, the following values are defined:

$$V_{HC} = V_A \frac{ywt}{100} \quad \text{Equation 5}$$

$$V_A = V_{HC} \frac{100}{ywt} \quad \text{Equation 6}$$

$$V_{Et} = V_{HC}\left(\frac{100}{ywt} - 1\right) \quad \text{Equation 7}$$

To calculate the volume of the ethanol fraction of the azeotrope ($V_{Et}$) for the first narrow fraction (column 3, Table 4):

$$ywt = 113.51 - 0.0443 * 95.9 - 0.001247 * 95.9^2 = 97.28$$

$$V_{Et} = 4.525 * \left(\frac{100}{97.28} - 1\right) = 0.102$$

The volume of ethanol combined with each narrow hydrocarbon fraction is shown in column 4 of Table 4. It is necessary to track the amount of ethanol added to the hydrocarbon component so that no more or less is used in the calculation than is added to the blend. In column 5 of Table 4, the cumulative amount of ethanol in the blend is tabulated. Note that the amount of ethanol that could combine with the sixth hydrocarbon fraction boiling at 184.9° F. is calculated to be 5.95%; however, only 1.049% ethanol remains from the total added. In column 6 of Table 4, the total azeotrope for each narrow fraction is calculated using Equation 4. For example, for the first narrow fraction:

4.525 ($V_{HC}$)+0.102 ($V_{Et}$)=4.627 ($V_A$)

This calculation method is continued for each narrow fraction, tracking the total amount of ethanol forming azeotropes until there is either no more ethanol or no more hydrocarbon fractions within the domain (i.e., boiling points between 90° F. and 275° F.). In the case of ethanol depletion, there will be excess hydrocarbon that does not form an azeotrope as shown in Table 4 for the narrow fraction with boiling point 184.9° F. In this example, the excess hydrocarbon from each narrow fraction is tabulated in column 7 of Table 4. In the case where no more hydrocarbon is available to form azeotrope, pure ethanol with boiling point 173° F. will form a single fraction in the blend.

The boiling point of the azeotrope formed from each narrow fraction is readily calculated using Equation 3. For example, the azeotrope boiling point for the first narrow fraction in Table 4 may be calculated as follows:

$$ybp = -28.33 + 1.532*95.9 - 0.002836*95.9^2 = 91.6$$

The azeotrope boiling points for the other narrow fractions are shown in column 8 of Table 4. For the narrow boiling fraction that boils at 184.9° F., there are two sub-fraction boiling points: a boiling point for the azeotrope (154.6° F. boiling point and 2.812% azeotrope) and a boiling point for the excess hydrocarbon (184.9° F. boiling point and 7.287% hydrocarbon).

Figure 4:
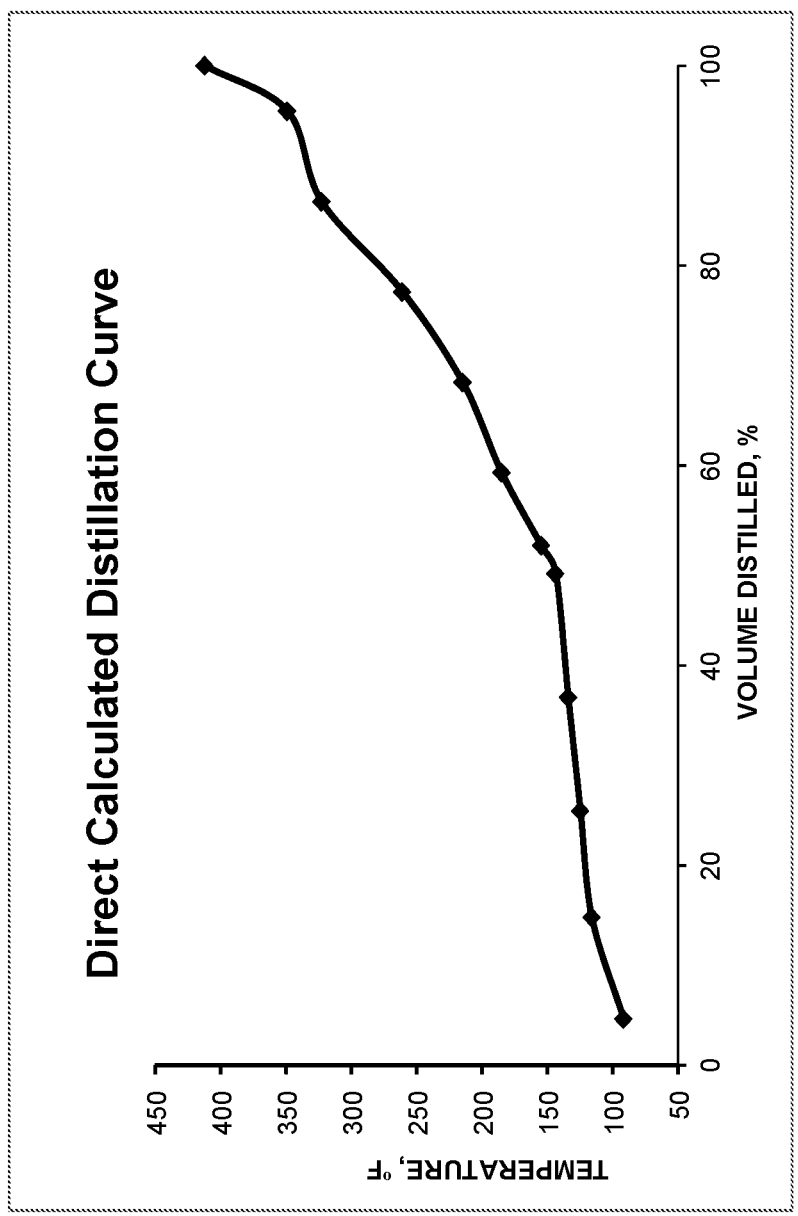
FIG. 4 illustrates a curve of temperature vs. cumulative volume.

The azeotrope amounts, excess hydrocarbon or excess oxygenate, and hydrocarbons with boiling points outside the range of azeotrope formation are correlated with their corresponding boiling points as shown in columns 6, 7, and 8 of Table 4. Using the data from Table 4, a curve of temperature vs. cumulative volume distilled may be generated (FIG. 4). The temperature axis (ordinate) is the boiling point (column 8, Table 4). The corresponding cumulative volume axis (abscissa) for each temperature was calculated by adding the values for total azeotrope volume (column 6, Table 4) and hydrocarbon remain volume (column 7, Table 4). For example, the total azeotrope volume for the azeotrope boiling point 91.6° F., 4.627 is added to the total azeotrope volume for the azeotrope boiling point 115.9° F. yielding a cumulative value of 14.785. The cumulative volume for each temperature is shown in column 3 of Table 5.

TABLE 5

| 1<br>Narrow<br>fraction<br>boiling<br>point | 2<br>Narrow<br>fraction<br>volume | 3<br>Cumulative<br>volume | 4<br>Standard<br>volume cut<br>points | 5<br>Volume<br>average<br>boiling<br>point | 6<br>Cubic Spline<br>interpolation<br>boiling<br>point |
|---|---|---|---|---|---|
| 91.6 | 4.627 | 4.627 | 5 | 93.4 | 92.6 |
| 115.9 | 10.158 | 14.785 | 10 | 116.1 | 116.2 |
| 124.7 | 10.653 | 25.438 | 20 | 124.7 | 125.0 |
| 134.0 | 11.352 | 36.790 | 30 | 133.6 | 133.6 |
| 143.5 | 12.386 | 49.176 | 40 | 141.8 | 134.3 |
| 154.6 | 2.812 | 51.988 | 50 | 159.1 | 169.1 |
| 184.9 | 7.287 | 59.275 | 60 | 202.0 | 208.7 |
| 214.7 | 9.05 | 68.325 | 70 | 245.4 | 249.8 |
| 260.7 | 9.05 | 77.375 | 80 | 308.0 | 299.3 |
| 322.7 | 9.05 | 86.425 | 90 | 345.1 | 344.0 |
| 348.8 | 9.05 | 95.475 | 100 | 406.0 | 412.0 |
| 412 | 4.525 | 100 | | | |

The eleven temperatures corresponding to volumes percent evaporated at: 0% (i.e. initial boiling point), 10%, 20%, 30%, 40%, 50%, 60%, 70%, 80%, 90% and 100% (i.e. final boiling point) are referred to as "standard cut points" and used to describe the distillation properties of hydrocarbon blending components and blends with oxygenates.

To generate a smooth curve, the temperatures at the common distillation points (e.g., initial boiling point, $T_{10}$, $T_{20}$, $T_{30}$, $T_{40}$, $T_{50}$, $T_{60}$, $T_{70}$, $T_{80}$, $T_{90}$, and final boiling point) are utilized. For example, to provide the standard distillation temperature vs vol % distilled correlation, the narrow fractions are combined and/or divided to provide the standard volume cut points as shown in column 4 of Table 5. The boiling points of the standard volume fractions may be obtained in various ways. As an example, the volume weighted arithmetic average of the combined or divided narrow fractions may be combined with the volume of another fraction to give the standard volume fraction: the volume of the first narrow fraction, 4.627, is combined with a portion of the volume of the second fraction, 0.373 (i.e., 0.373=5.000, the volume of the first standard cut point, minus 4.627), to generate the standard volume fraction of 5 (column 4, Table 5). The boiling temperature ($Tib_p$) may be calculated as follows:

$$T_{ibp} = \frac{(4.627*91.6 + 0.373*115.9)}{5} = 93.4$$

where 4.627 is the total azeotrope of the first narrow fraction (column 6, Table 4); 91.6 is the boiling point of the first narrow fraction (column 1, Table 5); the amount needed from the second fraction to make up the 5% standard cut point is 0.373; and 115.9 is the azeotrope boiling point of the second narrow fraction (column 8, Table 4). The second standard cut point ($T_{10}$) is obtained by combining the remaining volume from the second fraction, 9.785% (=10.158−0.373), with 0.215% (10−9.785) of the third fraction to generate the second standard cut point fraction with boiling point 116.1 calculated as follows:

$$T_{10} = \frac{(9.785*115.9 + 0.215*124.7)}{10} = 116.1$$

The boiling temperatures of the remaining standard volume cut points may be calculated similarly (column 5, Table 5), taking into consideration that the volumes of all the narrow fractions are included in one or more of the standard cut point fractions. Alternately, the data in columns 1 and 3 of Table 5 may be considered a smooth function and the standard volume cut points interpolated by the method of cubic splines (see, e.g., Numerical Recipes, Press, et al., University of Cambridge Press 1986, page 86) with the results given in column 6 of Table 5.

Figure 5:
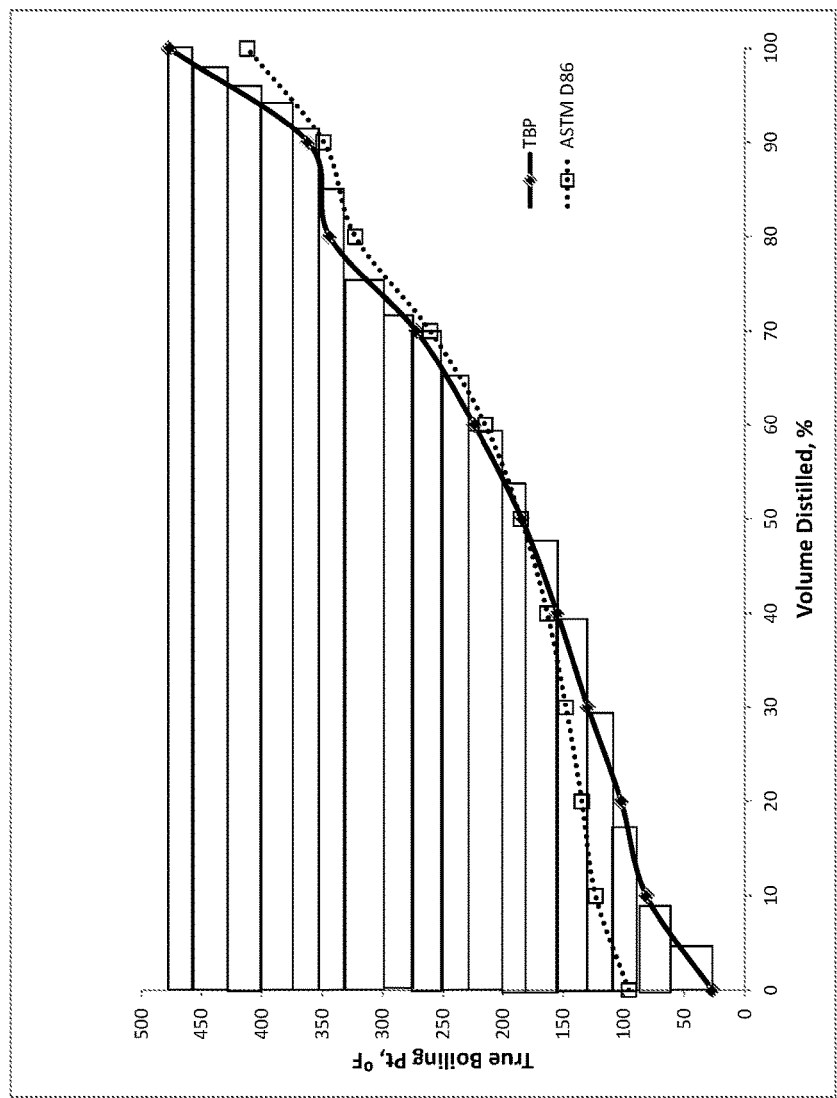
FIG. 5 illustrates a TBP curve for a hydrocarbon and its division into narrow fractions based on components boiling at 25° F. increments (e.g., pseudocomponents).

Additional embodiments of the methods described herein include, but not limited to, using a TBP curve. For example, the ASTM D86 distillation curve may be converted to a TBP curve before dividing the curve into narrow fractions. FIG. 5 illustrates the TBP curve for a hydrocarbon and its division into narrow fractions based on pseudocomponents boiling at 25° F. increments. Also, the relationship for the azeotrope composition may be the vol % of hydrocarbon in the azeotrope instead of wt %. Such conversions between wt % and vol % using appropriate densities are known to those skilled in the art. Alternate methods such as curve fitting, interpolation, and the like for dividing the boiling curve and reconstructing the curve after including the azeotropes may also be used for the methods of the invention. Additionally, other characterizations of a petroleum component boiling curve, for example, simulated distillation by gas chromatography as described by ASTM D3710 ("Standard Test Method for Boiling Range Distribution of Gasoline and Gasoline Fractions by Gas Chromatography") which provides higher resolution of temperature vs vol % distilled may also be employed by the methods described herein.

Figure 6:
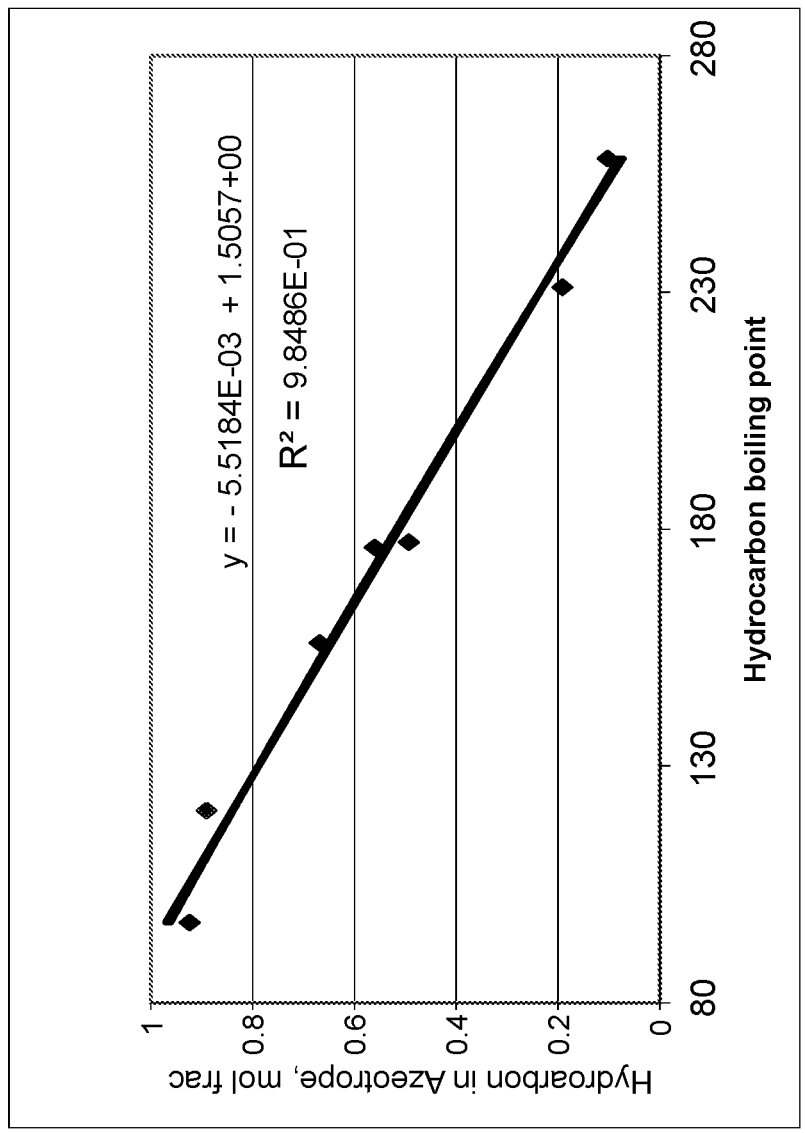
FIG. 6 illustrates a relationship between an azeotrope composition and the boiling point of the hydrocarbon in the azeotrope expressed as the mole fraction (mol fr) of the hydrocarbon in the azeotrope.

In another embodiment of the methods described herein, the relationship between the azeotrope composition and the boiling point of the hydrocarbon in the azeotrope as exemplified by Equation 2 may be expressed as the mole fraction (mol fr) of the hydrocarbon in the azeotrope instead of wt % as illustrated by Equation 8:

$$y(\text{mol fr}) = c_0 + c_1 * x \qquad \text{Equation 8}$$

where y(mol fr) is the mole fraction of the individual hydrocarbon in the azeotrope, x is the boiling temperature of the individual hydrocarbon, and $c_o$ and $c_1$ are coefficients of the equation. FIG. 6 illustrates the relationship for ethanol azeotropes. The coefficients are $c_0$ is 1.506 and $c_1$ is −0.005518, and the $R^2$ value is 0.98486 and were determined by least squares regression with y(mol fr) as the dependent variables and the corresponding individual hydrocarbon boiling temperatures as the independent variables, x.

Figure 7:
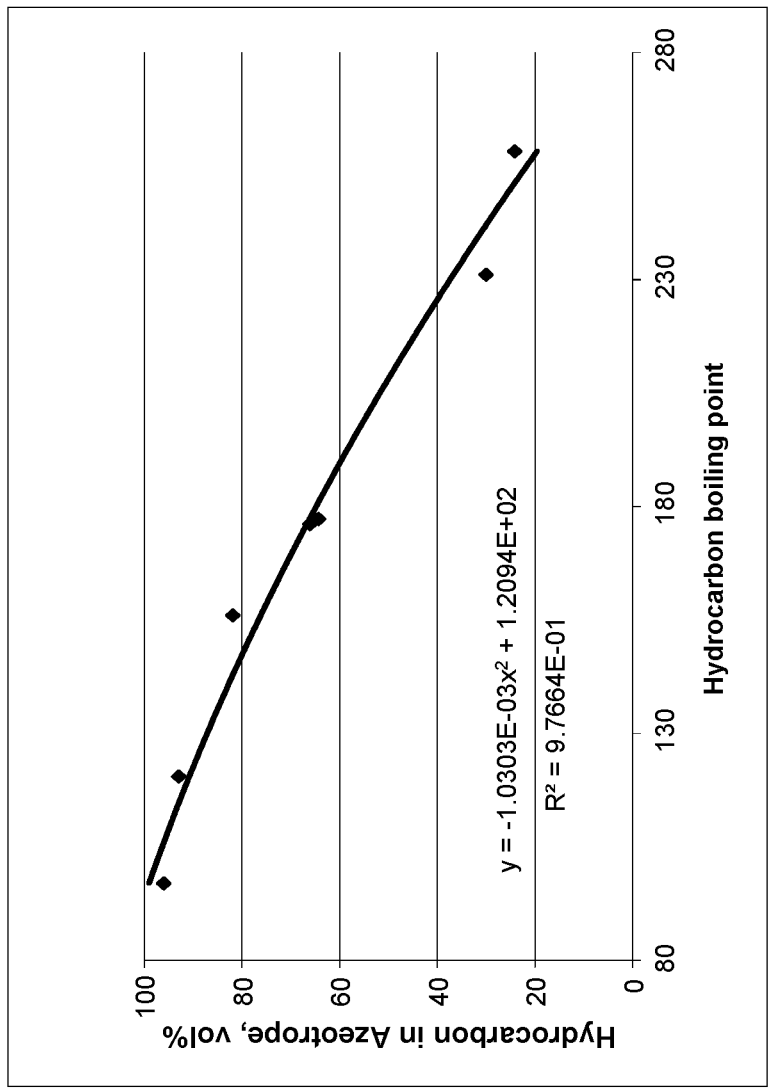
FIG. 7 illustrates an azeotrope composition expressed as vol % of a hydrocarbon in the azeotrope and as a function of the hydrocarbon boiling point.
Figure 8:
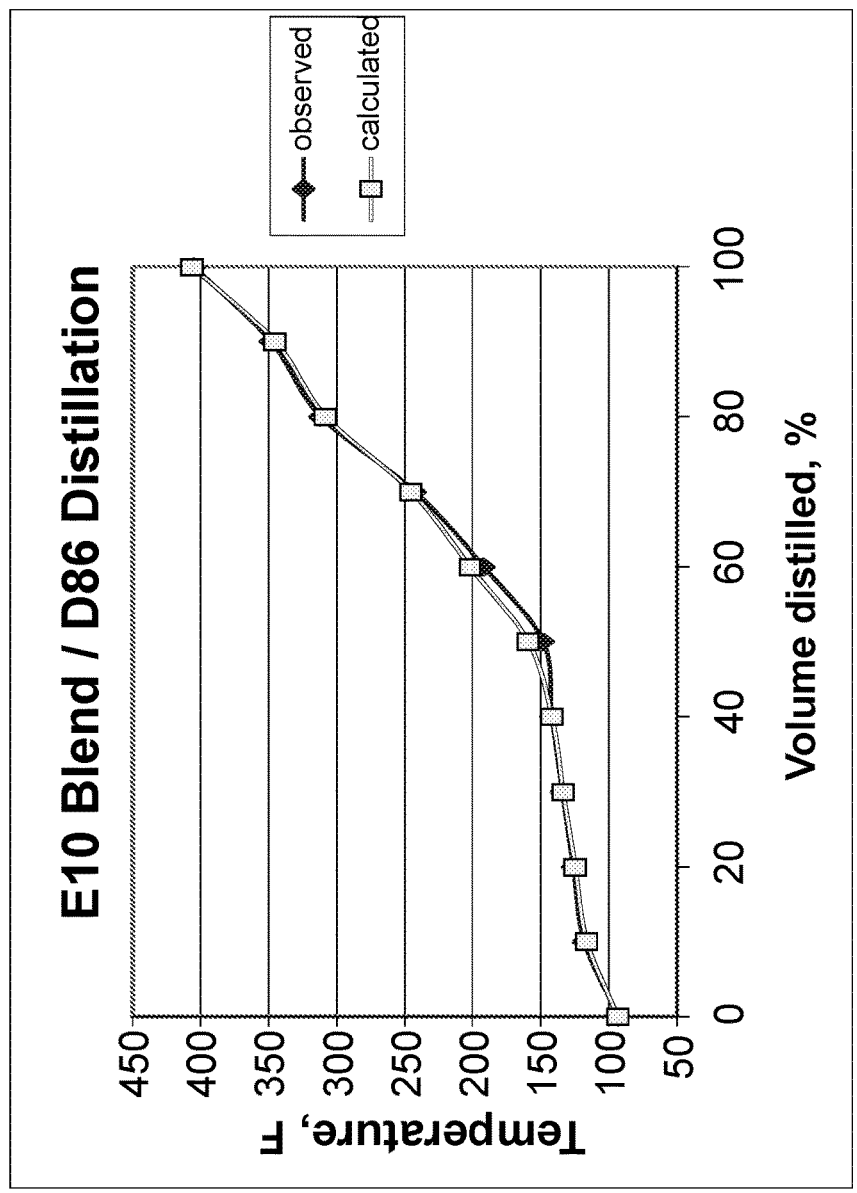
FIG. 8 is a plot of observed distillation characteristics and calculated distillation characteristics for a fuel blend containing gasoline and 10 vol % fuel grade ethanol.
Figure 9:
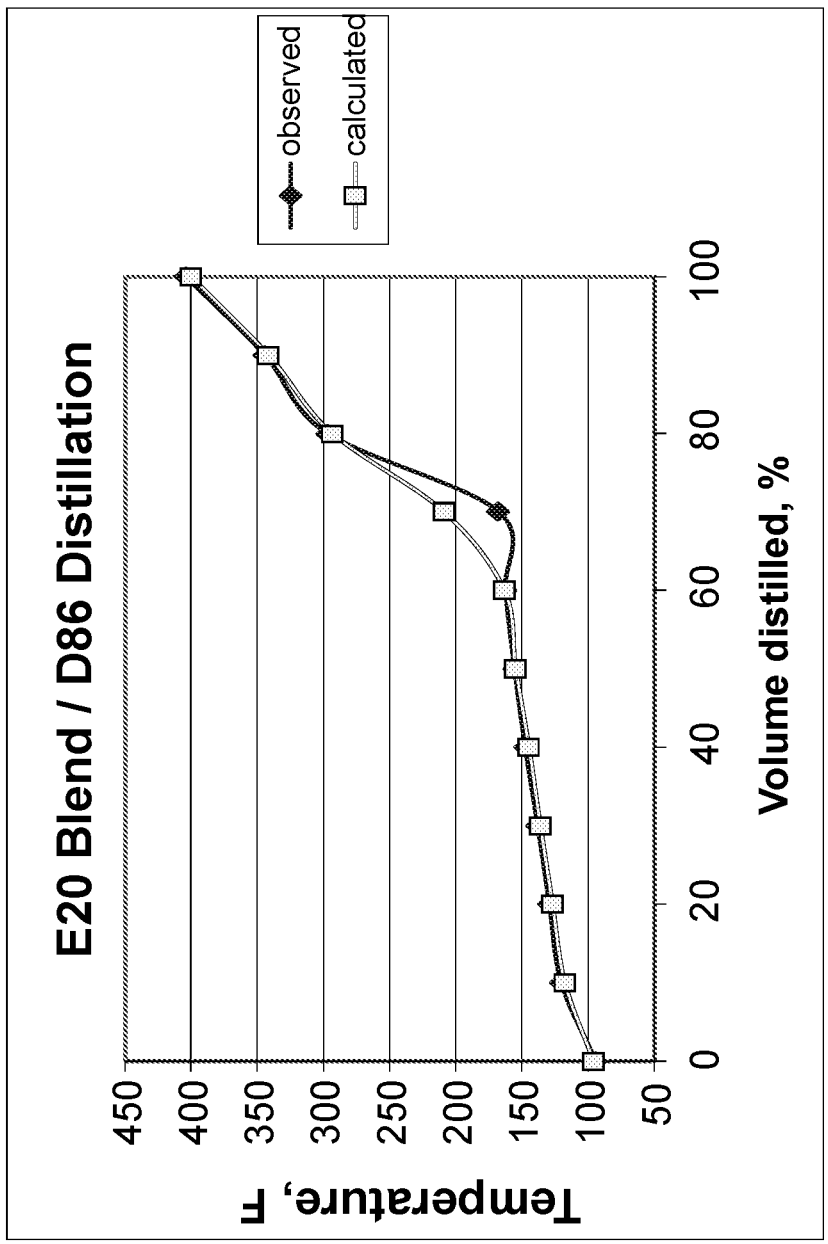
FIG. 9 is a plot of observed distillation characteristics and calculated distillation characteristics for a fuel blend containing gasoline and 20 vol % fuel grade ethanol.
Figure 10:
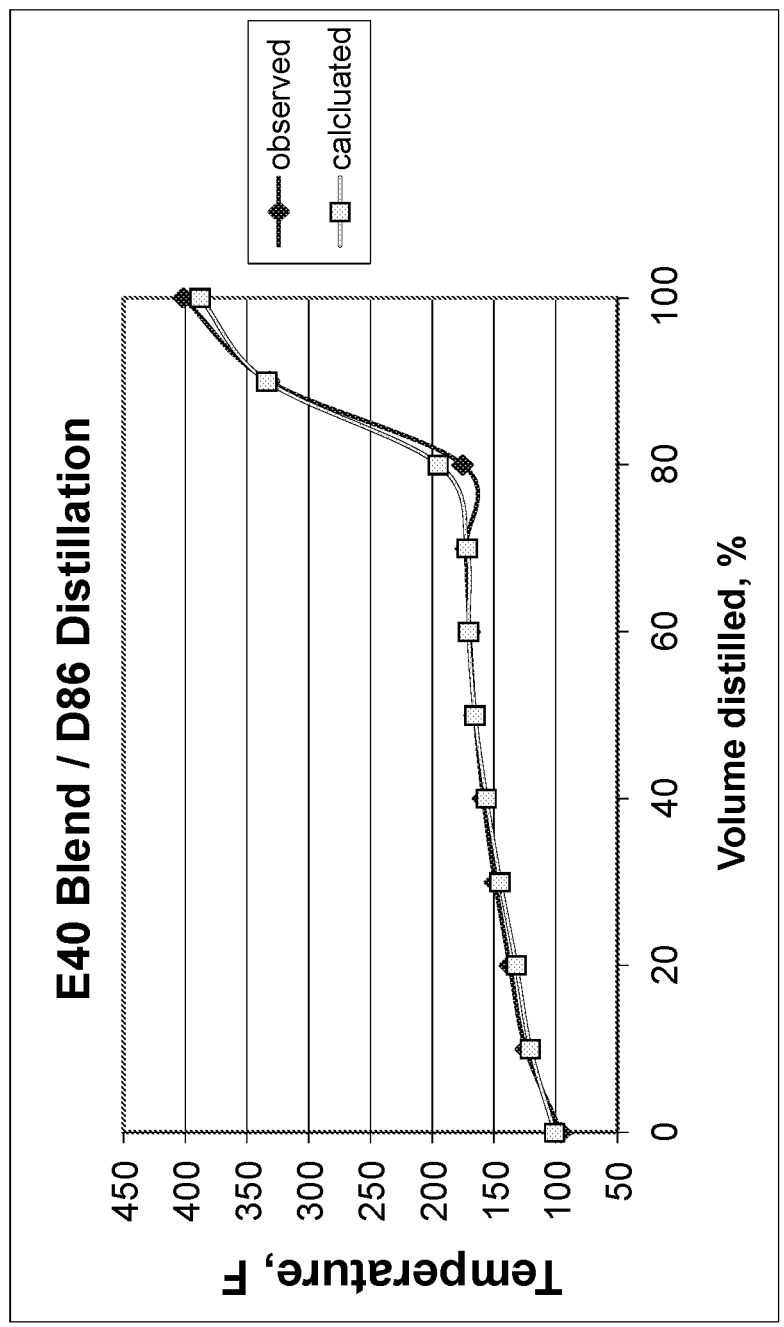
FIG. 10 is a plot of observed distillation characteristics and calculated distillation characteristics for a fuel blend containing gasoline and 40 vol % fuel grade ethanol.
Figure 11:
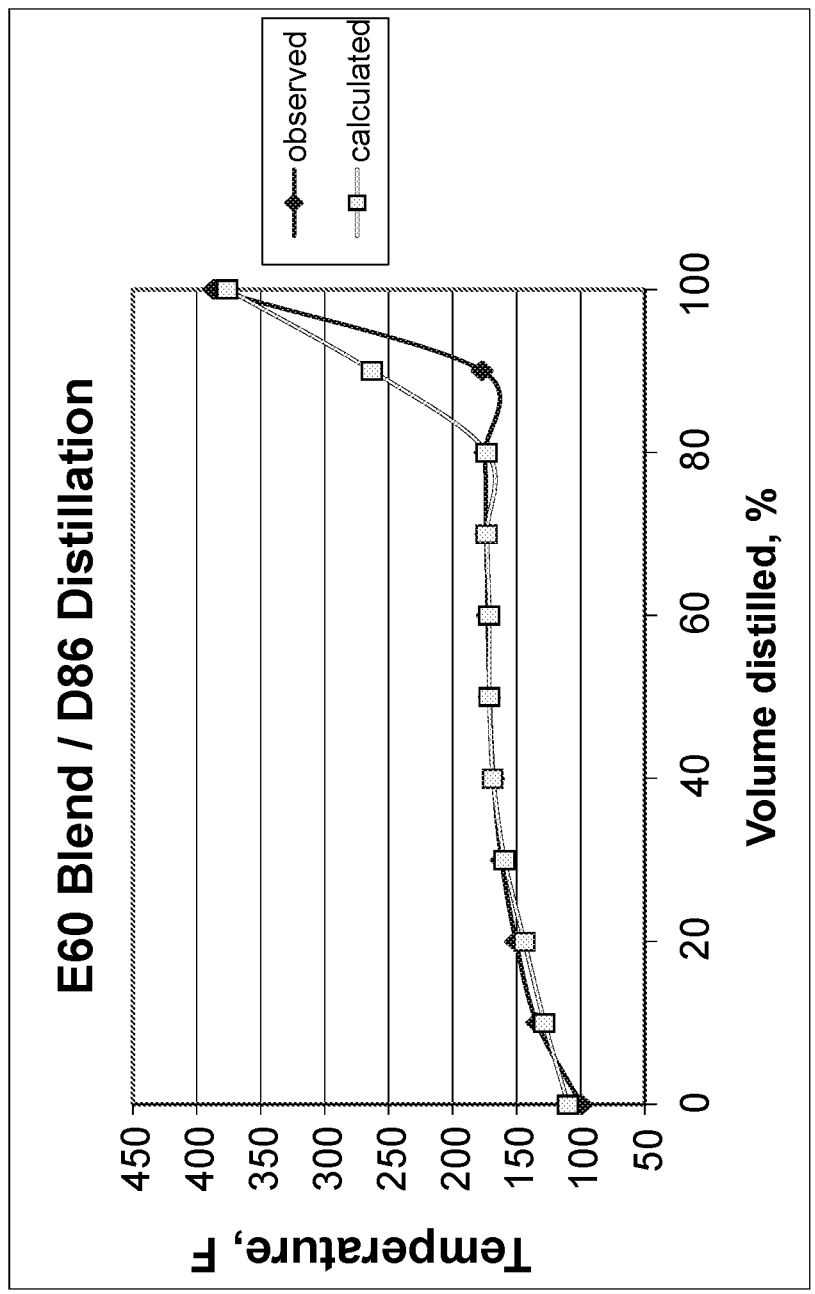
FIG. 11 is a plot of observed distillation characteristics and calculated distillation characteristics for a fuel blend containing gasoline and 60 vol % fuel grade ethanol.

In another embodiment, the azeotrope composition may be expressed as the vol % of the hydrocarbon in the azeotrope and as a function of the hydrocarbon boiling point as illustrated by Equation 9:

$$y(\text{vol}) = d_0 + d_1 x + d_2 x^2 \qquad \text{Equation 9}$$

where y(vol) is the vol % of the hydrocarbon in the azeotrope, x is the boiling temperature of the individual hydrocarbons, and $d_0$, $d_1$, and $d_2$ are coefficients of the equation. FIG. 7 illustrates the relationship for the ethanol azeotrope composition. The coefficients are $d_0$ is 120.94, $d_1$ is −0.12638, and $d_2$ is −0.001030, and the $R^2$ value is 9.766 and were determined by least squares regression with y(vol) as the dependent variables and the corresponding individual hydrocarbon boiling temperatures and their squares as the independent variables, x and $x^2$.

The selection of the relationship between azeotrope composition and hydrocarbon boiling point is a matter of convenience for the calculation and the degree of goodness of fit to the known azeotropic data. As exemplified herein, the relationships demonstrated a good fit with coefficients of determination ($R^2$) greater than 0.97.

Distillations illustrating the methods of this invention were performed using blend stocks with various amounts of fuel grade ethanol containing 95 vol % ethanol and 5 vol % hydrocarbon denaturant, and the distillation data for the hydrocarbon component shown in Table 2. FIGS. 8 to 11 demonstrate comparisons between observed distillations and the distillation characteristics calculated using the methods described herein. FIGS. 8, 9, 10, and 11 illustrate distillations of the fuel blends containing 10, 20, 40, and 60 vol %, respectively (i.e., E10, E20, E40, and E60) of the fuel grade ethanol. FIGS. 8 to 11 demonstrate agreement between observed distillation results and the calculated distillation characteristics. For the blends containing lower concentrations of ethanol (e.g., 10 and 20 vol %), the calculated temperatures match the observed azeotrope boiling temperatures. The blends containing higher concentrations of ethanol (e.g., 40 and 60 vol %) show the ethanol boiling at both its azeotrope temperatures and its normal boiling point (173° F.) because hydrocarbon is not available to form azeotropes. The largest deviations between the observed and calculated boiling temperatures are at the steep slope in the curve where experimental variability is the highest.

In these examples, the hydrocarbon blending component distillation curve was characterized by ASTM D86 data. As stated herein, it is well known to those skilled in the art that other distillation characterizations such as TBP (ASTM D285) or conversion of ASTM D86 data to TBP (see, e.g., Perry's Chemical Engineers' Handbook, 8th edition, Green, D. W. and Perry, R. H, Chapter 13, "Distillation," Section 13.10 "Petroleum and Complex Mixture Distillation," McGraw-Hill, New York, 2008) and simulated distillation (ASTM D2892) may be used to calculate distillation properties of a final mixture based on the distillation properties of its constituent components. In addition, the mathematical method of splines may be used to obtain smooth curves for either the division of a curve into narrow components or the combination of a collection of narrow components into a composite curve.

EXAMPLES

The present invention is further defined in the following Examples. It should be understood that these Examples, while indicating embodiments of the invention, are given by way of illustration only. From the description herein and these Examples, one skilled in the art can ascertain the essential characteristics of this invention, and without departing from the spirit and scope thereof, can make various changes and modifications of the invention to adapt it to various uses and conditions.

Example 1

Using the methods described herein, the distillation characteristics for azeotropic mixtures of isobutanol fuel blends can be determined.

Using the data in Tables 2 and 6, the relationship between the hydrocarbon composition of the azeotrope, a continuous, monotonic function of the boiling temperature of the individual hydrocarbon, and a domain within specified maximum and minimum boiling temperatures of the individual hydrocarbon component was determined. The data for the binary azeotrope may be found, for example, in Handbook of Chemistry and Physics (67th edition, CRC Press, 1986, page D-18).

TABLE 6

| | | Binary Azeotrope | | |
|---|---|---|---|---|
| Hydrocarbons | Hydrocarbon boiling point (° F.) | Boiling point (° F.) | Hydrocarbon concentration (wt %) | Hydrocarbon concentration (vol %) |
| n-Hexane | 156.02 | 154.94 | 97.5 | 97.9 |
| Cyclohexane | 177.35 | 172.94 | 86 | 86.4 |
| Benzene | 176.18 | 174.74 | 92.6 | 92.0 |
| Cylcohexene | 180.86 | 176.9 | 85.8 | 85.7 |
| Methyl Cylcopentane | 161.6 | 159.8 | 95 | 95.3 |
| n-Heptane | 209.21 | 195.44 | 73 | 76.0 |
| Methyl Cylcohexane | 213.44 | 198.68 | 68 | 68.9 |
| Toluene | 231.26 | 214.16 | 55 | 53.1 |
| 2,2,4-Trimethyl pentane | 210.74 | 197.6 | 73 | 75.8 |
| 2,5,-Dimethyl hexane | 228.56 | 209.66 | 58 | 61.5 |
| cis-1,3-Dimethyl Cyclohexane | 249.26 | 215.96 | 44 | 45.1 |
| Ethyl Benzene | 277.07 | 224.96 | 20 | 18.8 |
| p-Xylene | 281.12 | 224.78 | 11.4 | 10.7 |

The wt % compositions of the azeotropes were converted to vol % using the densities of the hydrocarbon compounds and isobutanol. The relationship between the hydrocarbon composition of the isobutanol azeotrope and the individual hydrocarbon boiling point was calculated using the quadratic function of Equation 10:

$$yvl = e_0 + e_1 x + e_2 x^2 \quad \text{Equation 10}$$

where yvl is the vol % of hydrocarbon in the azeotrope, x is the boiling temperature of the hydrocarbon, and $e_0$, $e_1$, and $e_2$ are coefficients of the equation. The relationship was determined by a standard least squares regression with the azeotrope hydrocarbon vol % as the dependent variable and the boiling point of the individual hydrocarbon and its square as the independent variables (i.e., data in Tables 2 and 6). The vol % hydrocarbon for each azeotrope in Table 6 was calculated from its wt % using the densities of the individual hydrocarbon and isobutanol. A continuous function was needed to allow interpolation of azeotrope hydrocarbon compositions between compositions of known azeotropes. Additionally, a monotonic function was needed to avoid ambiguity, for example, more than one possible azeotrope composition for a specific hydrocarbon boiling point.

Figure 12:
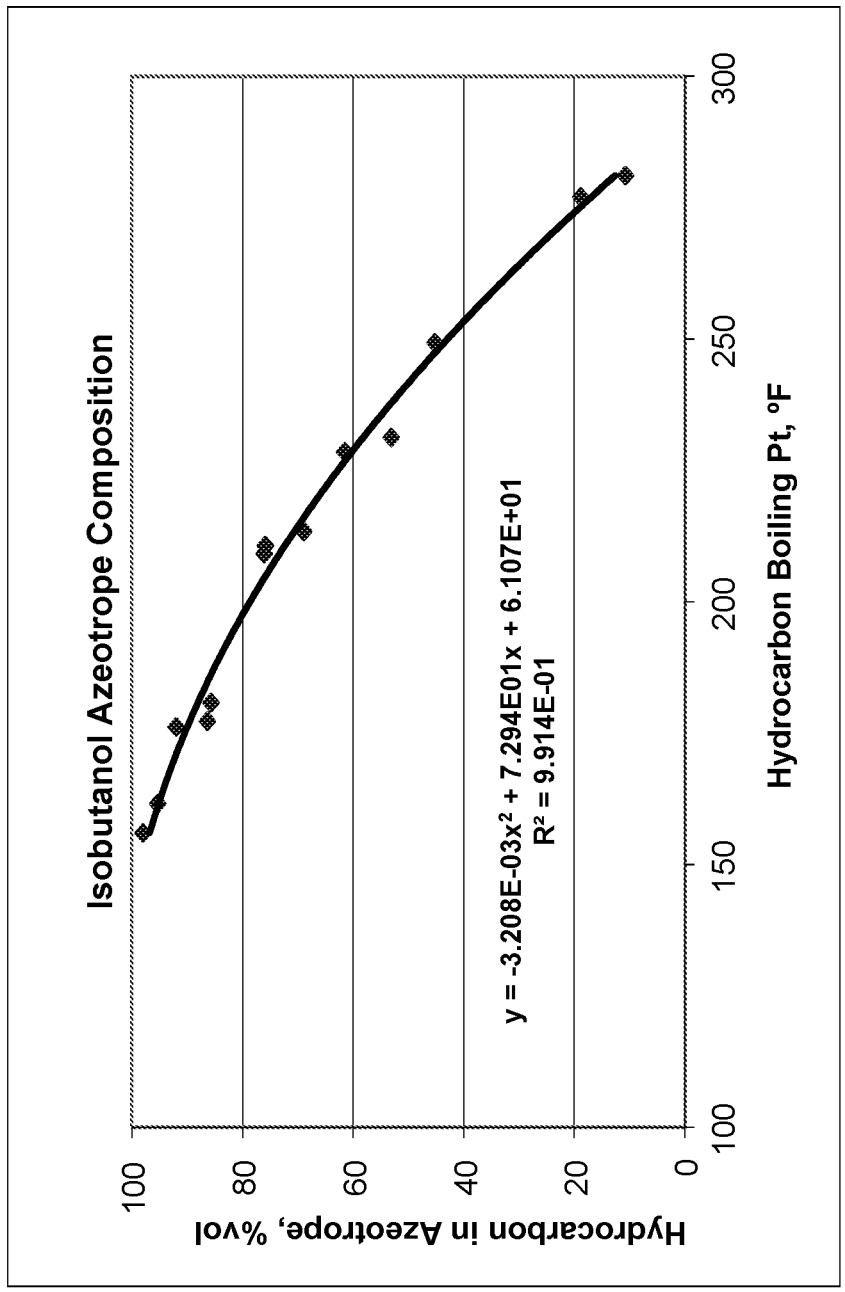
FIG. 12 illustrates a relationship between a hydrocarbon composition of an isobutanol azeotrope and a domain within specified maximum and minimum boiling temperatures of the individual hydrocarbon component.

FIG. 12 illustrates the relationship for the isobutanol azeotrope composition. The domain of the boiling temperature of the hydrocarbon variable is 156° F. to 290° F. inclusive (x-axis). The coefficients are $e_0$ is 61.07, $e_1$ is 0.7294, and $e_2$ is −0.003208, and the $R^2$ value is 0.9914. At the domain minimum, the vol % of hydrocarbon is 61.07+0.7294*156−0.003208*156²=96.8%; and at the domain maximum is 61.07+0.7294*290−0.003208*290²=2.8%. Thus, the range of the function is between 0% and 100% for these specified minimum and maximum boiling temperatures of hydrocarbons.

The second relationship between the boiling point of the azeotrope and a domain between specified maximum and minimum boiling temperatures of the hydrocarbon component was determined. The quadratic function of Equation 11 was used to determine the mathematical relationship between the boiling point of an isobutanol azeotrope and the individual hydrocarbon boiling point:

$$ybp = g_0 + g_1 x + g_2 x^2 \quad \text{Equation 11}$$

where ybp is the boiling temperature of the azeotrope, x is the boiling temperature of the hydrocarbon, and $g_0$, $g_1$, and $g_2$ are coefficients of the equation. The relationship was determined by a standard least squares regression with the azeotrope boiling point as the dependent variable and the boiling point of the individual hydrocarbon and its square as the independent variables (i.e., data in Tables 2 and 6). A continuous function was needed to allow interpolation of azeotrope boiling points between boiling points of known azeotropes. Additionally, a monotonic function was needed to avoid ambiguity, for example, more than one possible azeotrope boiling point for a specific hydrocarbon boiling point.

Figure 13:
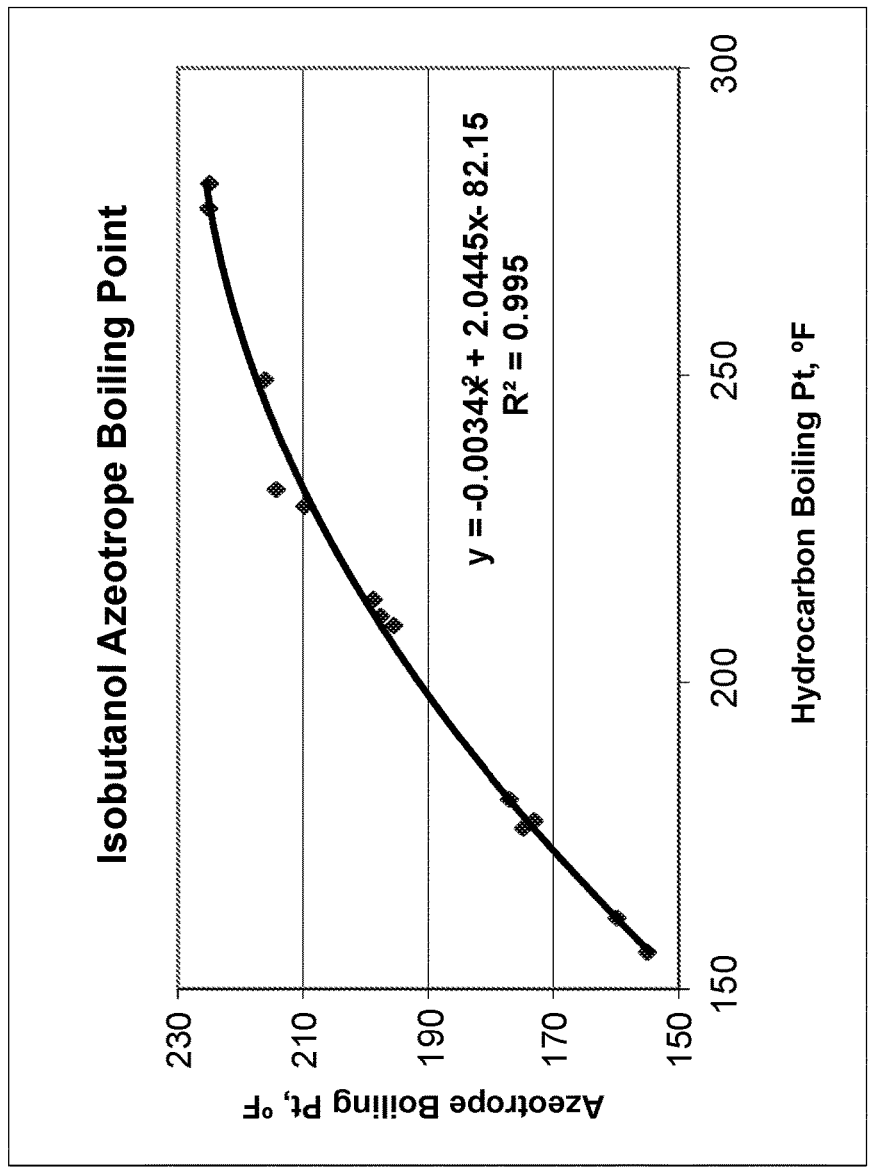
FIG. 13 illustrates a relationship between the boiling point of an isobutanol azeotrope and a domain between specified maximum and minimum boiling temperatures of the individual hydrocarbon component.

FIG. 13 illustrates the second relationship for an isobutanol azeotrope. The domain of the boiling temperature of hydrocarbon variable is 156° F. to 290° F. inclusive (x-axis). The coefficients are $g_0$ is −82.15, $g_1$ is 2.0445, and $g_2$ is −0.003382, and the $R^2$ value is 0.995. At the domain maximum, the azeotrope boiling point is −82.15+2.0445*290−0.003382*290²=226.3° F. which is below the boiling point of isobutanol that is 226.4° F. Thus, the range of the function is between 0% and 100% and the maximum boiling point is below the oxygenate for these specified minimum and maximum boiling temperatures of hydrocarbons.

The boiling curve of the isobutanol blend was generated as described by the methods herein. The boiling curve of the hydrogen blending component shown in Table 7 was divided into narrow boiling ranges at volume intervals to represent hydrocarbon species in the blend.

TABLE 7

Hydrocarbon Blending Component for Isobutanol

| Vol % Distilled | Temperature (° F.) |
|---|---|
| Initial Boiling Point | 108.86 |
| 10 | 136.76 |
| 20 | 152.24 |
| 30 | 169.88 |
| 40 | 191.66 |
| 50 | 215.24 |
| 60 | 237.02 |
| 70 | 258.08 |
| 80 | 290.12 |
| 90 | 326.84 |
| Final Boiling Point | 356 |

A narrow fraction consisting of the first 5 vol % was assigned a boiling point of 108.86° F.; a second narrow fraction of 10 vol % was assigned a boiling point of 136.76° F.; a third narrow fraction of 10 vol % was assigned a boiling point of 152.24° F., a fourth narrow fraction of 10 vol % was assigned a boiling point of 169.88° F., a fifth narrow fraction of 10 vol % was assigned a boiling point of 191.66° F., a sixth narrow fraction of 10 vol % was assigned a boiling point of 215.24° F., a seventh narrow fraction of 10 vol % was assigned a boiling point of 237.02° F., an eight narrow fraction of 10 vol % was assigned a boiling point of 258.08° F., a ninth narrow fraction of 10 vol % was assigned a boiling point of 290.14° F., a tenth narrow fraction of 10 vol % was assigned a boiling point of 326.84° F., and an eleventh narrow fraction of 5 vol % was assigned a boiling point of 356° F. The narrow fractions with boiling points between 156° F. and 290° F. then represent hydrocarbons that may form azeotropes with isobutanol. The minimum and maximum limits of azeotrope formation are the domain in which the mathematical correlations are valid (i.e., monotonic and continuous within reasonable extrapolation and interpolation of the known azeotrope data). The data are shown in columns 1 and 2 of Table 8.

TABLE 8

| 1 Boiling point (° F.) | 2 Narrow fraction volume | 3 70% Hydrocarbon of blend | 4 30% Isobutanol of blend | 5 Cumulative isobutanol in blend | 6 Total azeotrope | 7 Hydrocarbon remain | 8 Azeotrope boiling point |
|---|---|---|---|---|---|---|---|
| 108.86 | 5 | 3.5 | 0.0 | 0.0 | 0.0 | 3.5 | 108.86 |
| 136.76 | 10 | 7.0 | 0.0 | 0.0 | 0.0 | 7.0 | 136.76 |
| 152.24 | 10 | 7.0 | 0.0 | 0.0 | 0.0 | 7.0 | 152.24 |
| 169.88 | 10 | 7.0 | 0.576 | 0.576 | 7.576 | 0 | 167.65 |
| 191.66 | 10 | 7.0 | 1.431 | 2.007 | 8.431 | 0 | 185.56 |
| 215.24 | 10 | 7.0 | 3.080 | 5.087 | 10.080 | 0 | 201.33 |

TABLE 8-continued

| 1<br>Boiling<br>point<br>(° F.) | 2<br>Narrow<br>fraction<br>volume | 3<br>70%<br>Hydrocarbon<br>of blend | 4<br>30%<br>Isobutanol<br>of blend | 5<br>Cumulative<br>isobutanol<br>in blend | 6<br>Total<br>azeo-<br>trope | 7<br>Hydro-<br>carbon<br>remain | 8<br>Azeotrope<br>boiling<br>point |
|---|---|---|---|---|---|---|---|
| 237.02 | 10 | 7.0 | 6.028 | 11.115 | 13.028 | 0 | 212.56 |
| 258.08 | 10 | 7.0 | 12.639 | 23.754 | 19.639 | 0 | 220.36 |
|  |  |  | Excess<br>isobutanol | 30.0 | 6.246 | 0 | 226.4 |
| 290.12 | 10 | 7.0 | 0 |  | 0 | 7.0 | 290.12 |
| 326.84 | 10 | 7.0 | 0 |  | 0 | 7.0 | 326.84 |
| 356 | 5 | 3.5 | 0 |  | 0 | 3.5 | 356 |

The amount of hydrocarbon in each fraction that forms an azeotrope with the oxygen or nitrogen compound in the final blend was then determined. For a blend of 70% petroleum blending component and 30% isobutanol, the amount of hydrocarbon in each fraction available to form azeotrope is 70% of the narrow fraction (i.e., narrow fraction volume times 0.70) as shown in column 3 of Table 8. The maximum amount of isobutanol that can combine with a particular narrow fraction is given by its boiling point (i.e., similar to an individual hydrocarbon) and the relationship determined by Equation 10. The distillation data for the hydrocarbon blending component is shown in Table 7.

The maximum volume of isobutanol was determined, for example, by a simple addition of volumes within each narrow fraction:

$$V_A = V_{HC} + V_{Iso} \quad \text{Equation 12}$$

where $V_A$ is the volume of azeotrope, $V_{HC}$ is the volume of hydrocarbon fraction of the azeotrope, and $V_{Iso}$ is the volume of the isobutanol fraction of the azeotrope. Using Equation 10, the following values were defined:

$$V_{HC} = V_A \frac{yvl}{100} \quad \text{Equation 13}$$

$$V_A = V_{HC} \frac{100}{yvl} \quad \text{Equation 14}$$

$$V_{Iso} = V_{HC}\left(\frac{100}{yvl} - 1\right) \quad \text{Equation 15}$$

The boiling temperatures of the first three narrow fractions, 108.86, 136.76, and 152.24, are outside (i.e., below) the domain for azeotrope formation, 156° F. to 290° F. So no isobutanol azeotropes form with these fractions. To calculate the volume of the isobutanol fraction of the azeotrope ($V_{Iso}$) for the fourth narrow fraction (column 4, Table 8):

$$yvl = 61.07 + 0.7294*169.88 - 0.003208*169.88^2 = 992.4$$

$$V_{Iso} = 7.0*\left(\frac{100}{92.4} - 1\right) = 0.576$$

The volume of the isobutanol fraction for each narrow fraction is shown in column 5 of Table 8. In column 6 of Table 8, the total azeotrope for each narrow fraction is calculated using Equation 12.

This calculation method was continued for each narrow fraction tracking the total amount of isobutanol forming azeotropes until there was either no more isobutanol or no more hydrocarbon fractions within the domain. Column 5 of Table 8 tracks the cumulative amount of isobutanol in the blend and column 7 of Table 8 tracks the amount of hydrocarbon that is not combined in the azeotrope of each narrow fraction. For isobutanol, the fractions boiling below 156° F. do not form azeotropes, and there is isobutanol remaining when the boiling point of the hydrocarbon fraction exceeded the domain of azeotrope formation (i.e., 290.12° F. compared to 290° F.). The remaining isobutanol distills as the pure alcohol with a boiling point 226.4° F., and the boiling points of remaining hydrocarbon fractions were unaffected.

The boiling point of the azeotrope formed from each narrow fraction was readily calculated using Equation 11. For example, the fourth narrow fraction in Table 8 may be calculated as follows:

$$ybp = -82.15 + 2.0445*169.88 - 0.003382*169.88^2 = 185.56 \quad \text{Equation 11}$$

The azeotrope boiling points for the other narrow fractions are shown in column 8 of Table 8. The azeotrope amounts, excess hydrocarbon or excess oxygenate, and hydrocarbons with boiling points outside the range of azeotrope formation are correlated with their corresponding boiling points as shown in columns 6, 7, and 8 of Table 8. The data from columns 6, 7, and 8 of Table 8 are shown in columns 1 and 2 of Table 9 with column 3 as the cumulative volume that is correlated with the boiling point in column 1. Using the data from columns 1 and 3 of Table 9, a curve of temperature vs. cumulative volume was generated. The temperature is the azeotrope boiling point (column 8, Table 8). The cumulative volume for each temperature was calculated by adding the values for total azeotrope (column 6, Table 8) or hydrocarbon remain (column 7, Table 8). For example, the hydrocarbon remain value for the azeotrope boiling point 108.86° F. is 3.5 and is added to the hydrocarbon remain value for the azeotrope boiling point 136.76° F. yielding a cumulative value of 10.5. The cumulative volume for each temperature is shown in column 3 of Table 9.

TABLE 9

| 1<br>Narrow<br>fraction<br>boiling<br>point | 2<br>Narrow<br>fraction<br>volume | 3<br>Cumulative<br>volume | 4<br>Standard<br>volume cut<br>points | 5<br>Volume<br>average<br>boiling<br>point |
|---|---|---|---|---|
| 108.86 | 3.5 | 3.5 | 5 | 117.23 |
| 136.76 | 7.0 | 10.5 | 10 | 143.73 |
| 152.24 | 7.0 | 17.5 | 20 | 163.80 |
| 167.65 | 7.576 | 25.076 | 30 | 187.47 |
| 185.56 | 8.431 | 33.507 | 40 | 202.49 |
| 201.33 | 10.080 | 43.587 | 50 | 212.56 |
| 212.56 | 13.028 | 56.614 | 60 | 218.58 |
| 220.36 | 19.639 | 76.253 | 70 | 220.36 |

TABLE 9-continued

| 1<br>Narrow<br>fraction<br>boiling<br>point | 2<br>Narrow<br>fraction<br>volume | 3<br>Cumulative<br>volume | 4<br>Standard<br>volume cut<br>points | 5<br>Volume<br>average<br>boiling<br>point |
|---|---|---|---|---|
| 226.4 | 6.247 | 82.5 | 80 | 241.03 |
| 290.12 | 7.0 | 89.5 | 90 | 310.32 |
| 326.84 | 7.0 | 96.5 | 100 | 347.25 |
| 356 | 3.5 | 100 | | |

To generate a curve with temperatures at the distillation cut points (e.g., initial boiling point, $T_{10}$, $T_{20}$, $T_{30}$, $T_{40}$, $T_{50}$, $T_{60}$, $T_{70}$, $T_{80}$, $T_{90}$, and final boiling point), data from Table 9 were utilized. For example, to provide the standard distillation temperature vs vol % distilled correlation, the narrow fractions were combined and/or divided to provide the standard volume cut points as shown in column 4 of Table 9. The boiling points of the standard volume fractions may be obtained in various ways. As an example, the volume weighted arithmetic average of the combined or divided narrow fractions was combined with the volume of another fraction to give the standard volume fraction: the volume of the first narrow fraction, 3.5, was combined with a portion of the volume of the second fraction, 1.5 (i.e., 3.5+1.5=5.0 or 5.0−3.5=1.5), to generate the standard volume fraction of 5.0 (column 2, Table 9). The boiling temperature ($T_{ibp}$) may be calculated as follows:

$$T_{ibp} = \frac{(3.5*108.86 + 1.5*136.76)}{5} = 117.23$$

where 3.5 is the hydrocarbon remain value of the first narrow fraction (column 7, Table 8); 108.86 is the boiling point of the first narrow fraction (column 1, Table 8); 1.5 is part of the second fraction; and 136.76 is the boiling point of the second narrow fraction (column 1, Table 8). The boiling temperatures of the remaining standard volume fractions were calculated similarly (column 5, Table 9), taking into consideration that the volumes of the narrow fractions are included in one or more of the standard cut point fractions.

Figure 14:
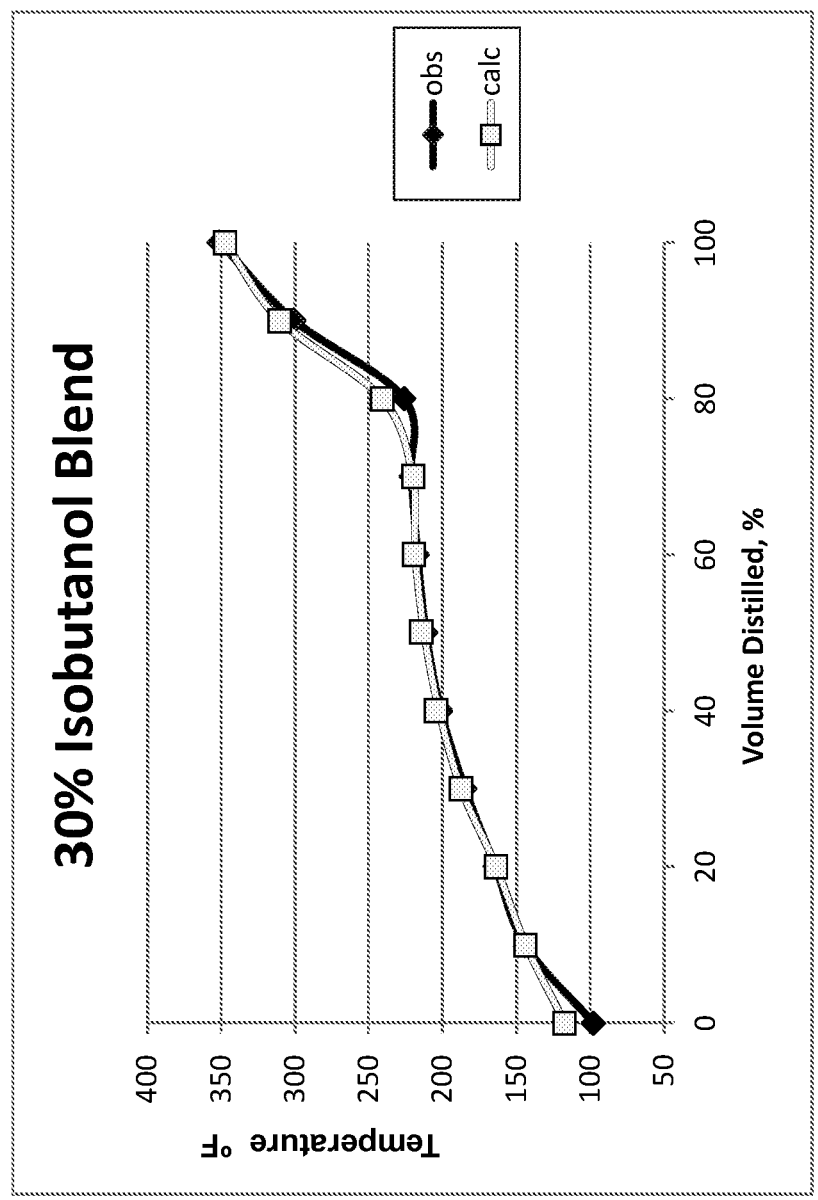
FIG. 14 illustrates a standard distillation curve plotting standard volume cut points (x-axis) versus volume average boiling points (y-axis).

A standard distillation curve was plotted by using data from columns 4 and 5 of Table 9 and is shown in FIG. 14 as well as the observed distillation of the blend measured by the ASTM D86 method.

Example 2

Using Equation 9 for the volume percent composition of ethanol azeotropes, Equation 3 for the boiling points of ethanol azeotropes, Equation 10 for the volume percent composition of isobutanol azeotropes, and Equation 11 for the boiling points of isobutanol azeotropes, a distillation curve for a blend of 5.0 vol % ethanol, 8.3 vol % isobutanol, and 86.7 vol % hydrocarbon component with distillation properties listed in Table 10 was calculated according to the method described herein. The domains of the equation are unaltered, that is, for ethanol: the minimum temperature is 90° F. and the maximum temperature is 275° F. and for isobutanol: the minimum temperature is 156° F. and the maximum temperature is 290° F.

TABLE 10

Hydrocarbon Blending Component for Isobutanol

| Vol % Distilled | Temperature (° F.) | Narrow Fraction Volume |
|---|---|---|
| Initial Boiling Point | 74.7 | 2.5 |
| 5 | 88.9 | 7.5 |
| 10 | 118.6 | 10 |
| 20 | 153.8 | 10 |
| 30 | 182.5 | 10 |
| 40 | 205.1 | 10 |
| 50 | 226.3 | 10 |
| 60 | 247.4 | 10 |
| 70 | 268.7 | 10 |
| 80 | 293.6 | 10 |
| 90 | 317.4 | 10 |
| 95 | 332.5 | 7.5 |
| Final Boiling Point | 363.9 | 2.5 |

In this example, two additional cut points have been included, 5% and 95% distilled. The volumes assigned to the narrow fractions are shown in Table 10. This modification of the narrow fraction volumes accommodates "13-point" distillation data that are commonly reported in the ASTM D86 test method. The boiling points and volumes of the hydrocarbon are tabulated in order to calculate the formation of azeotropes and their boiling points as shown in Table 11. Columns 1, 2, 3, 4 and 5 contain the information for the hydrocarbon portion and ethanol portion of the blend, and columns 6, 7, 8, 9 and 10 contain information for the isobutanol portion, total azeotrope amount, hydrocarbon not in azeotropes and corresponding boiling points. Data was calculated using the methods as described in Example 1.

TABLE 11

| 1<br>Boiling<br>point<br>(° F.) | 2<br>Narrow<br>fraction<br>volume | 3<br>86.7%<br>Hydrocarbon<br>of blend | 4<br>5.0%<br>Ethanol<br>of blend | 5<br>Cumulative<br>ethanol<br>in blend | 6<br>8.3%<br>Isobutanol<br>of blend | 7<br>Cumulative<br>Isobutanol<br>in blend | 8<br>Total<br>azeo-<br>trope | 9<br>Hydro-<br>carbon<br>remain | 10<br>Boiling<br>point |
|---|---|---|---|---|---|---|---|---|---|
| 74.7 | 2.5 | 2.1675 | 0 | 0 | 0 | 0 | 0.0 | 2.1675 | 74.7 |
| 88.9 | 7.5 | 4.335 | 0 | 0 | 0 | 0 | 0.0 | 4.335 | 88.9 |
| 118.6 | 10 | 6.5025 | 0.607 | 0.607 | 0 | 0 | 7.110 | 0 | 112.1 |
| 153.8 | 10 | 8.67 | 2.571 | 3.178 | 0 | 0 | 11.240 | 0 | 137.8 |
| 182.5 | 10 | 8.67 | 1.822 | 5.00 | 0.796 | 0.796 | 11.288 | 0 | 153.5, 178.3 |
| 205.1 | 10 | 8.67 | 0 | | 2.780 | 3.576 | 11.450 | 0 | 194.9 |

TABLE 11-continued

| 1<br>Boiling point (° F.) | 2<br>Narrow fraction volume | 3<br>86.7% Hydrocarbon of blend | 4<br>5.0% Ethanol of blend | 5<br>Cumulative ethanol in blend | 6<br>8.3% Isobutanol of blend | 7<br>Cumulative Isobutanol in blend | 8<br>Total azeotrope | 9<br>Hydrocarbon remain | 10<br>Boiling point |
|---|---|---|---|---|---|---|---|---|---|
| 226.3 | 10 | 8.67 | 0 |  | 4.724 | 8.30 | 12.382 | 1.012 | 207.3, 226.3 |
| 247.4 | 10 | 8.67 | 0 |  | 0 |  | 0 | 8.67 | 247.4 |
| 268.7 |  | 8.67 | 0 |  | 0 |  | 0 | 8.67 | 268.7 |
| 293.6 | 10 | 8.67 | 0 |  | 0 |  | 0 | 8.67 | 293.6 |
| 317.4 | 10 | 6.5025 | 0 |  | 0 |  | 0 | 6.5025 | 317.4 |
| 332.5 | 7.5 | 4.335 | 0 |  | 0 |  | 0 | 4.335 | 332.5 |
| 363.9 | 2.5 | 2.1675 | 0 |  | 0 |  | 0 | 2.1675 | 363.9 |

Azeotropes forming with ethanol are considered first because the domain minimum is lower than for isobutanol (i.e., 90° F. as compared to 156° F. for isobutanol) and the boiling points will be lower than isobutanol azeotropes. The first azeotrope forms with ethanol with the hydrocarbon narrow fraction boiling at 118.6° F. For the hydrocarbon narrow fraction boiling at 182.5° F., a portion, 3.178%, forms azeotropes with ethanol until the amount of ethanol is exhausted. The remainder of the hydrocarbon, 5.492%, forms azeotropes with isobutanol because the hydrocarbon fraction boils above the minimum temperature for isobutanol azeotrope formation (182.5° F.>156° F.). Therefore, there are two boiling points listed in column 10 for this fraction, the lower boiling point (153.5° F.) corresponding to the ethanol azeotrope and the higher (178.3° F.) corresponding to the isobutanol azeotrope.

Figure 15:
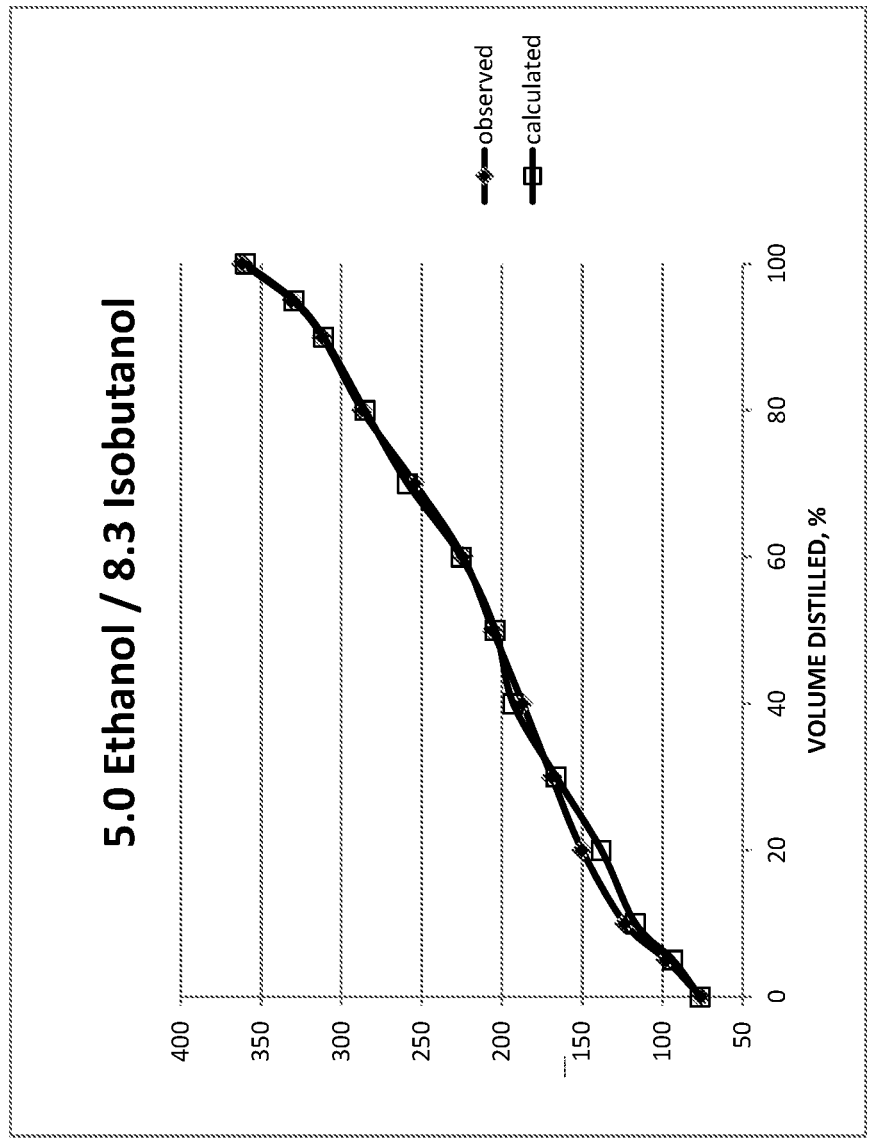
FIG. 15 illustrates a distillation curve for an ethanol/isobutanol/hydrocarbon blend.

The data from columns 8, 9 and 10 of Table 11 are collected in Table 12 to calculate the volume weighted average boiling points at standard cut points for a 13-point distillation. Volume average boiling points were calculated in same manner as described in Example 1 and the distillation curve is shown in FIG. 15.

TABLE 12

| 1<br>Narrow fraction boiling point | 2<br>Narrow fraction volume | 3<br>Cumulative volume | 4<br>Standard volume cut points | 5<br>Volume average boiling point |
|---|---|---|---|---|
| 74.7 | 2.1675 | 2.1675 | 2.5 | 76.6 |
| 88.9 | 4.335 | 6.5025 | 7.5 | 93.5 |
| 112.1 | 7.110 | 13.612 | 10 | 116.8 |
| 137.8 | 11.240 | 24.853 | 10 | 138.1 |
| 153.5 | 5.00 | 29.853 | 10 | 166.3 |
| 178.3 | 6.288 | 36.141 | 10 | 193.0 |
| 194.9 | 11.450 | 47.591 | 10 | 204.1 |
| 207.3 | 12.382 | 59.973 | 10 | 225.3 |
| 226.3 | 1.012 | 60.985 | 10 | 258.8 |
| 247.4 | 8.67 | 69.655 | 10 | 285.3 |
| 268.7 | 8.67 | 78.325 | 10 | 311.1 |
| 293.6 | 8.67 | 86.995 | 7.5 | 329.5 |
| 317.4 | 6.5025 | 93.4975 | 2.5 | 359.7 |
| 332.5 | 4.335 | 97.8325 |  |  |
| 363.9 | 2.1675 | 100 |  |  |

The examples demonstrate that distillation properties calculated by the methods described herein are in agreement with measured distillation properties. That is, the functions for azeotrope compositions and boiling points of complex hydrocarbon mixtures with, for example, alcohols such as ethanol and isobutanol may be used to predict the distillation properties of hydrocarbon-oxygenate blends. Therefore, these methods may be used to produce hydrocarbon-oxygenate blends that meet fuel requirements.

The calculations described herein including determination of the relationships of azeotrope composition (step a) and azeotrope boiling point (step b), division of the boiling curve (step c), calculation of azeotrope compositions and azeotrope boiling points (step d), and correlation of volume fractions and boiling points to determine distillation characteristics (step e) are amenable to programming using spreadsheets (e.g., Microsoft Excel®) or general formula translation compliers (e.g., Fortran, C, C+, etc.).

It will be appreciated by those skilled in the art that, while the present invention has been described herein by reference to particular methods, materials, and specific examples, the scope of the present invention is not limited thereby, and extends to all other means, methods and materials suitable for practice of the present invention.

What is claimed is:

1. A process for determining the distillation characteristics of a liquid petroleum product that contains an azeotropic mixture of an oxygenated or nitrogen-containing component and at least one petroleum blending component comprising:
   (a) defining a relationship between the boiling points of hydrocarbons of the liquid petroleum product and the concentration of each such hydrocarbon in an azeotrope with the oxygenated or nitrogen-containing component;
   (b) defining a relationship between the boiling points of the hydrocarbons and the boiling points of the azeotropes;
   (c) generating a boiling point curve of narrow volume percent distillate fractions and distillation temperature for each such volume percent distillate fraction;
   (d) for each volume percent distillate fraction from step (c)
      (i) determining the total concentration of hydrocarbons in the distillate fraction;
      (ii) determining the amounts of the azeotropic mixture and of the oxygenated or nitrogen-containing component in each such volume percent distillate fraction and
      (iii) determining the boiling point of the azeotropic mixture that corresponds to each such volume percent; and
   (e) correlating for each volume percent distillate fraction the amount of the azeotropic mixture in the distillate fraction from step (d)(ii) with the boiling point from step (d)(iii), and combining such correlations to thereby determine the distillation characteristics of the liquid petroleum product.

2. The process of claim 1, wherein the oxygenated component is an alcohol, ester, ketone, ether, ester alcohol, keto-alcohol, ether alcohol, aldehyde, ether aldehyde, or aldehyde alcohol.

3. The process of claim 2, wherein the oxygenated component is at least one alcohol.

4. The process of claim 3, wherein the oxygenated component is ethanol.

5. The method of claim 3, wherein the oxygenated component is an isomer of butanol.

6. The method of claim 5, wherein the isomer of butanol is 1-butanol, 2-butanol, isobutanol, tert-butanol.

7. The process of claim 1, wherein the liquid petroleum product is a gasoline.

8. The process of claim 2, wherein the oxygenated component is a mixture of one or more oxygenates.

9. The process of claim 8, wherein the oxygenated component is a mixture of one or more alcohols.

10. The process of claim 1, wherein the nitrogen containing component is an amine, amide, nitrile, nitro ester, nitrate ester, nitrite ester, cyclic nitrogen compound, amino alcohol, ether amine, or poly amine.

11. The process of claim 10, wherein the nitrogen containing component is a mixture of one or more nitrogen containing components.

12. The process of claim 1, wherein the nitrogen containing component is a mixture of one or more nitrogen containing components and one or more oxygenated components.

* * * * *